(12) United States Patent
Salazar

(10) Patent No.: US 10,456,579 B2
(45) Date of Patent: Oct. 29, 2019

(54) DIRECT ELECTRICAL STIMULATION DELIVERY SYSTEM FOR THE TREATMENT OF VISUAL DISEASE

(71) Applicant: NOVA OCULUS CANADA MANUFACTURING ULC, Fergus (CA)

(72) Inventor: Alfonso Salazar, Topanga, CA (US)

(73) Assignee: Nova Oculus Canada Manufacturing ULC, Fergus, Ontario (CA)

( * ) Notice: Subject to any disclaimer, the term of this patent is extended or adjusted under 35 U.S.C. 154(b) by 0 days.

(21) Appl. No.: 15/969,107

(22) Filed: May 2, 2018

(65) Prior Publication Data
US 2018/0318586 A1    Nov. 8, 2018

Related U.S. Application Data

(60) Provisional application No. 62/500,190, filed on May 2, 2017.

(51) Int. Cl.
*A61N 1/36* (2006.01)
*A61N 1/04* (2006.01)
(Continued)

(52) U.S. Cl.
CPC ..... *A61N 1/36046* (2013.01); *A61N 1/36014* (2013.01); *A61N 1/0492* (2013.01); *A61N 1/0526* (2013.01); *A61N 1/205* (2013.01)

(58) Field of Classification Search
None
See application file for complete search history.

(56) References Cited

U.S. PATENT DOCUMENTS 3,464,416 A * 9/1969 Williams ........... A61N 1/36014
                                                        600/26
4,989,605 A    2/1991 Rossen
(Continued)

FOREIGN PATENT DOCUMENTS

WO    WO 2017/048731 A1    3/2017

OTHER PUBLICATIONS

Anastassiou, G., Article, "Transpalpebral electrotherapy for dry age-related macular degeneration (AMD): An exploratory trial", Restorative Neurology and Neuroscience, vol. 31 (2013) pp. 571-578 (9 pgs).
(Continued)

*Primary Examiner* — Kennedy Schaetzle
(74) *Attorney, Agent, or Firm* — Stinson LLP

(57) ABSTRACT

An electrotherapeutic system for treating a visual disease is disclosed. The system includes a signal generator configured to generate a treatment waveform comprising a series of current pulses. Preferably, the current pulses have a peak current amplitude of 200 microamps or less. The system also includes a headset applicator comprising a headband and a headset. The headset has a magnetic slot configured to be mounted to a magnetic mount of the headband. The headset includes left and right eyecup electrodes each of which has a contact surface that is positioned for contact with a skin surface within left and right eye regions, respectively. Preferably, the contact surface of each of the left and right eyecup electrodes comprises an upper contact pad and a lower contact pad that have a total area in the range of about 1.10 cm$^2$ to about 1.80 cm$^2$. The headset is connectable to the signal generator and configured to deliver the treatment waveform to one or both of the left and right electrodes.

25 Claims, 15 Drawing Sheets

(51) Int. Cl.
*A61N 1/05* (2006.01)
*A61N 1/20* (2006.01)

(56) References Cited

U.S. PATENT DOCUMENTS

| | | | |
|---|---|---|---|
| 5,395,398 | A | 3/1995 | Rogozinski |
| 5,522,864 | A | 6/1996 | Wallace et al. |
| 6,035,236 | A | 3/2000 | Jarding et al. |
| 6,275,735 | B1 | 8/2001 | Jarding et al. |
| 7,158,834 | B2 | 1/2007 | Paul, Jr. |
| 7,251,528 | B2 | 7/2007 | Harold |
| 8,434,168 | B2 | 5/2013 | Paulson |
| 8,612,008 | B2 | 12/2013 | Kirsch et al. |
| 9,199,080 | B2 | 12/2015 | Gekeler et al. |
| 9,956,405 | B2 * | 5/2018 | Goldwasser ......... A61N 1/0476 |
| 2003/0233137 | A1 | 12/2003 | Paul |
| 2004/0176820 | A1 | 9/2004 | Paul |
| 2005/0004625 | A1 | 1/2005 | Chow |
| 2013/0053733 | A1 | 2/2013 | Korb et al. |
| 2015/0018927 | A1 | 1/2015 | Warschewske |
| 2015/0032170 | A1 | 1/2015 | Gilman et al. |
| 2015/0112153 | A1 | 4/2015 | Nahum |
| 2017/0266445 | A1 | 9/2017 | O'Clock |
| 2017/0266446 | A1 | 9/2017 | O'Clock |

OTHER PUBLICATIONS

Shinoda, K., Article, "Transcutaneous Electrical Retinal Stimulation Therapy for Age-Related Macular Degeneration", The Open Ophthalmology Journal, vol. 2, (2008) pp. 132-136 (5 pgs).
Dor, H, Article, "Beitrage zur Electrotherapie der Augenkrankheiten" (Translation: "Contributions for Electrotherapy of Eye Diseases"), Albrecht von Graefes Archiv fur Opthalmologie, vol. 19 (1873) pp. 316-352 (37 pgs) (This reference is written in German).
Derby, H., Article "On the Possible Retardation of Retinitis Pigmentosa", Trans Am Ophthalmol Soc., vol. 4 (1886) pp. 217-227 (11 pgs).
O'Clock, G.D., et al., Article, "Electrotherapeutic Device/Protocol Design Considerations for Visual Disease Applications," Proceedings of the 31$^{st}$ Annual International IEEE Engineering in Medicine and Biology Society Conference (EMBC '09), Sep. 2-6, 2009, Minneapolis, MN, pp. 2133-2136 (4 pgs).
McGehee, F, website blog, "How Does Microcurrent Therapy Work?", obtained from website "Wayback Machine" as visible on internet on Jul. 16, 2015, https://web.archive.org/web/20150716004702/http://www.machular-degeneration.net/about-microcurrent (2 pgs), downloaded from the internet on Oct. 13, 2016.
Kondrot, website blog, "Microcurrent Stimulation", obtained from website "Wayback Machine" as visible on internet on Mar. 31, 2015, https://web.archive.org/web/20150331174948/http://www.healingtheeye.com/microcurrent (4 pgs), downloaded from the internet on Oct. 13, 2016.
Grossman, M, website blog, "How Microcurrent Stimulation Could Help Eye Diseases", obtained from website "Wayback Machine" as visible on internet on Jun. 3, 2013, https://web.archive.org/web/20130603120513/http://www.naturaleyecare.com/blog/how-microcurrent-stimulation-help-eye-diseases (1 pg), downloaded from the internet on Oct. 13, 2016.
Ronald Trahn Associates, Inc., Press Release, "EBS Technologies Reports That a Clinical Study Published in Neurology Validates Electrical Brain Stimulation Technology Designed to Expand the Visual Field of Patients with Impaired Vision", published on the internet at http://venturebeat.com/2014/09/18/3bs-technologies-reports-that-a-clinical-study-published-in-neurology-validates-electrical-brain-stimulation-technology-designed-to-expand-the-visual-field-of-patients-with-impaired-vision published Sep. 18, 2014 (3 pgs), downloaded from the internet on Oct. 13, 2016.
Jarding, J. et al, Chapter 47 entitled "Biocurrent Therapy for Macular Degeneration" published in book titled *Bioelectromagnetic Medicine*, published by Marcel Dekker, Inc., New York, NY (2004), 2 title pages and pp. 771-780 (12 pgs).
O'Clock, G.D., Book, "Electrotherapeutic Devices: Principles, Design and Applications", Artech House Pub., Boston, MA (2007), the entire book is being submitted.
Yue, Lan, et al., "Retinal Stimulation Strategies to Restore Vision: Fundamentals and Systems", Progress in Retinal and Eye Research, vol. 53, pp. 21-47 (2016) (27 pgs).
Butterwick et al., "Tissue Damage by Pulsed Electrical Stimulation", IEE Transactions on Biomedical Engineering, vol. 54, No. 12, Dec. 2007 (8 pgs).
Cukjati et al., Chapter 31, "Electric Current Wound Healing", Bioelectromagnetic Medicine, P.J. Rosch and M. Markove, (eds), New York, Marcel Dekker, 2004, pp. 485-505 (21 pgs).
Zhao et al., "Electric Field-directed Cell Motility Involves Up-regulated Expression and Asymmetric Redistribution of the Epidermal Growth Factor Receptors and Is Enhanced by Fibronectin and Laminin", Molecular Biology of the Cell, vol. 10, pp. 1259-1276, Apr. 1999 (18 pgs).
Cheng et al., "The Effects of Electric Currents on ATP Generation, Protein Synthesis, and Membrane Transport in Rat Skin", Clinical Orthopedics and Related Research, vol. 171, pp. 264-271, 1982 (8 pgs).
Butterwick et al., "Dynamic Range of Safe Electrical Stimulation of the Retina", SPIE Proceeding, Ophthalmic Technologies XVI, SPIE vol. 6138 (2006) (8 pgs).
Michael et al., "Nutritional Supplementation, Electrical Stimulation and Age Related Macular Degeneration", Journal of Orthomolecular Medicine, vol. 8, No. 3, 1993 (4 pgs).
"Transcorneal Electrical Stimulation Therapy for Retinal Disease", downloaded on Dec. 7, 2017 from http://clinicaltrials.gov/ct2/show/record/NCT00804102 (7 pgs).
Allen, et al., "Macular Degeneration Treatment with Nutrients and Micro Current Electricity", Journal of Orthomolecular Medicine, vol. 13, No. 4, 1998 (4 pgs).
Humayn, et al., "Visual Perception Elicited by Electrical Stimulation of Retina in Blind Humans", Archives of Opthalmology, vol. 114, No. 1, Jan. 1996 (7 pgs).
International Search Report and Written Opinion dated Sep. 7, 2018 for related PCT/IS2018/000558 dated May 2, 2018 (8 pgs).

* cited by examiner

DIRECT ELECTRICAL STIMULATION DELIVERY SYSTEM FOR THE TREATMENT OF VISUAL DISEASE

CROSS-REFERENCE TO RELATED APPLICATIONS

This application is based on and claims priority to U.S. Provisional Application Ser. No. 62/500,190, filed on May 2, 2017, which is incorporated herein by reference in its entirety.

STATEMENT REGARDING FEDERALLY SPONSORED RESEARCH OR DEVELOPMENT

Not applicable.

BACKGROUND OF THE INVENTION

1. Field of the Invention

The present invention relates generally to systems and methods for electrical stimulation therapy, and more particularly to systems and methods that provide transpalpebral microcurrent electrotherapy for the treatment of age-related macular degeneration and other visual diseases.

2. Description of Related Art

Electrical stimulation therapy has emerged as a viable treatment modality for numerous diseases and disorders of the human body. One method of providing electrical stimulation therapy is to deliver microcurrent, which is typically defined as current below 1 milliamp (peak), to tissue on or near the area of the body to be treated. For example, microcurrent in the range of 100 microamps to 1,000 microamps (peak) has been applied to skin of an eye region, generating pulses of low current (microamps) in specific waveform patterns and well-defined frequency ranges for the treatment of age-related macular degeneration and other visual diseases. While a variety of devices have been developed to provide microcurrent stimulation to skin of an eye region, there are a number of problems associated with these devices.

For example, some devices require a practitioner to physically hold the tip of an electrical contact probe against one or more target points on the skin of an eye region in order to apply the microcurrent stimulation. Attempting to hold a contact probe in the delicate region of the eye for a typical treatment duration of 10 minutes or greater is difficult and very fatiguing. The physical body is not designed to hold devices in place for long durations of time. As a result, devices that rely on the practitioner's use of a contact probe are unstable due to the human fatigue factor. A related problem associated with the use of a contact probe is the potential risk to a patient. For example, if the practitioner loses his balance during a treatment session, the contact probe can be pressed too hard against the skin of the eye region causing discomfort or injury to the patient. Also, proper placement of the contact probe is entirely dependent on the skill of the practitioner performing the treatment. Inconsistent placement leads to differing results, causing ineffective treatments.

In order to address the human fatigue factor, devices have been developed in which one or more electrical contacts are held in position against the skin of an eye region of a patient. For example, some devices have a goggles-type design in which several electrical contacts are incorporated into the goggles and an elastic strap is placed around the patient's head. However, these devices may cause undue pressure to the skin of the eye region due to the elasticity of the strap and inaccurate adjustment levels. This increase in pressure can cause the electrical contacts to dig into the skin of the eye region resulting in discomfort to the patient.

Devices have also been developed in which one or more electrical contacts are incorporated into a type of eyeglass frame. However, the delivery of microcurrent stimulation using these devices is often not repeatable due to the fact that an eyeglass frame has large degrees of freedom and the placement of the electrical contacts on the skin of the eye region is inconsistent from one treatment session to the next. Hand held contact probes and goggles-type devices also suffer from this same repeatability problem.

Yet another problem with hand held contact probes, goggles-type devices, and eyeglass frame-type devices is that each of the electrical contacts comprises a point source having a relatively small surface area. The electrical properties of a point source are not optimal and it is believed that the internal energy transfer from a point source to targeted tissue within an eye region has not been thoroughly modeled. Inadequate surface area and a poor electrical model have resulted in ineffective treatment to patients suffering from visual disease.

Thus, there is a need for an improved delivery system that overcomes one or more of the problems set forth above and can be used to deliver microcurrent stimulation to skin of an eye region for the treatment of age-related macular degeneration and other visual diseases.

SUMMARY OF THE INVENTION

The present invention is directed to a direct electrical stimulation delivery system for use in the treatment of patients suffering from age-related macular degeneration and other visual diseases.

In one embodiment, the system includes a signal generator configured to generate a waveform comprising a series of current pulses (e.g., current pulses having a peak current amplitude of 200 microamps or less). The system also includes a headset that is connectable to the signal generator and configured to deliver the waveform to a skin surface within an eye region of a patient. The headset includes at least one eyecup electrode having a contact surface that is positioned for contact with the skin surface. The contact surface of the eyecup electrode has an area in the range of about 1.10 cm$^2$ to about 1.80 cm$^2$.

In another embodiment, the system includes a signal generator configured to generate a treatment waveform comprising a series of current pulses (e.g., current pulses having a peak current amplitude of 200 microamps or less). The system also includes a headset that is connectable to the signal generator and configured to deliver the waveform to a skin surface within an eye region of a patient. The headset includes at least one eyecup electrode having a contact surface comprising an upper contact pad and a lower contact pad. The upper contact pad comprises an arc that curves concave downward and is positioned for contact with an upper portion of the skin surface, and the lower contact pad comprises an arc that curves concave upward and is positioned for contact with a lower portion of the skin surface.

In another embodiment, the system includes a signal generator configured to generate a treatment waveform comprising a series of current pulses (e.g., current pulses having a peak current amplitude of 200 microamps or less).

The system also includes a headband having a magnetic mount. The system further includes a headset having a magnetic slot configured to be mounted to the magnetic mount of the headband. The headset includes a left eyecup electrode having a contact surface that is positioned for contact with a skin surface within a left eye region and, similarly, the headset includes a right eyecup electrode having a contact surface that is positioned for contact with a skin surface within a right eye region. The contact surface of each of the left and right eyecup electrodes has an area in the range of about 1.10 cm$^2$ to about 1.80 cm$^2$. The headset is connectable to the signal generator and configured to deliver the waveform to one or both of the left and right eyecup electrodes.

In yet another embodiment, the system includes a signal generator configured to generate a treatment waveform comprising a series of current pulses (e.g., current pulses having a peak current amplitude of 200 microamps or less). The system also includes a headband having a magnetic mount. The system further includes a headset having a magnetic slot configured to be mounted to the magnetic mount of the headband. The headset includes a left eyecup electrode having a contact surface that is positioned for contact with a skin surface within a left eye region and, similarly, the headset includes a right eyecup electrode having a contact surface that is positioned for contact with a skin surface within a right eye region. The contact surface of each of the left and right eyecup electrodes comprises an upper contact pad and a lower contact pad. The upper contact pad comprises an arc that curves concave downward and the lower contact pad comprises an arc that curves concave upward. The headset is connectable to the signal generator and configured to deliver the waveform to one or both of the left and right eyecup electrodes.

BRIEF DESCRIPTION OF THE DRAWINGS

Various exemplary embodiments of the present invention are described in detail below with reference to the attached drawing figures, wherein.

DETAILED DESCRIPTION OF EXEMPLARY EMBODIMENTS

The present invention is directed to a direct electrical stimulation delivery system for use in the treatment of patients suffering from age-related macular degeneration and other visual diseases. While the invention will be described in detail below with reference to various exemplary embodiments, it should be understood that the invention is not limited to the specific system configuration or methodologies of these embodiments. In addition, although the exemplary embodiments are described as embodying several different inventive features, one skilled in the art will appreciate that any one of these features could be implemented without the others in accordance with the present invention.

I. System Components

Figure 1:
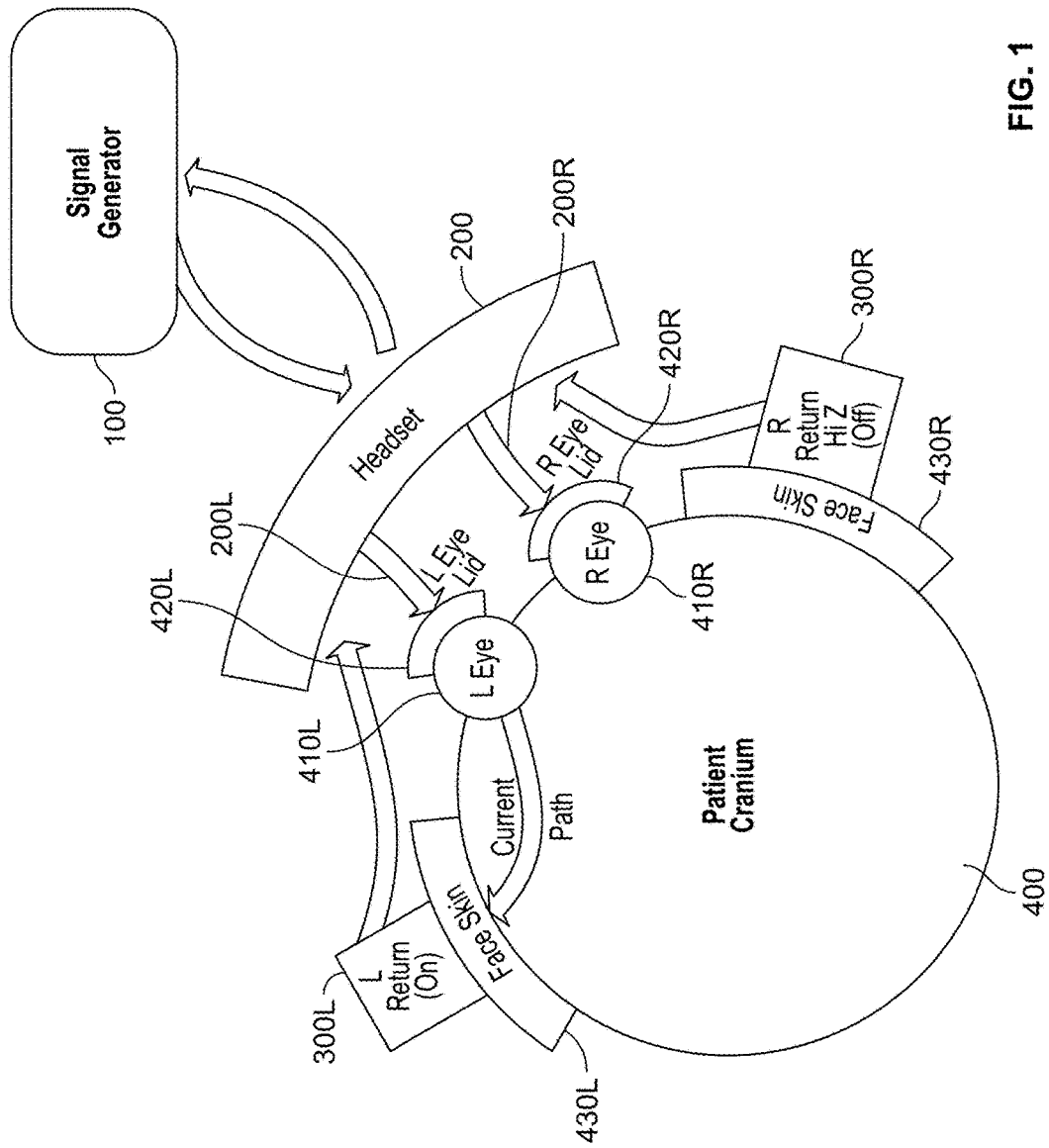
FIG. 1 is a diagram of a direct electrical stimulation delivery system in accordance with an exemplary embodiment of the present invention.

A diagram of a direct electrical stimulation delivery system in accordance with an exemplary embodiment of the present invention is shown in FIG. 1. As can be seen, the system generally includes a signal generator 100, a headset applicator 200 with left and right eyecup electrodes 200L and 200R, and left and right return electrodes 300L and 300R. The system is used to treat patients, such as the patient 400, suffering from age-related macular degeneration and other visual diseases. It should be noted that patient 400 has left and right eyes 410L and 410R, left and right eyelids 420L and 420R, and left and right temples 430L and 430R, which are shown diagrammatically in FIG. 1.

Signal generator 100 is programmed to generate a treatment waveform that is provided to headset applicator 200. Headset applicator 200 is the delivery system for the waveform and provides a stable platform for the alignment and consistent positioning of left and right eyecup electrodes 200L and 200R in contact with a skin surface within each of the left and right eye regions (which are generally shown as left and right eyelids 410L and 410R in FIG. 1). In an exemplary embodiment, left and right eyecup electrodes 200L and 200R each include upper and lower contact pads (described below) that contact the skin surface within an eye region at the following general locations: (a) the upper contact pad contacts a skin surface located below the upper bone of the eye socket and above the upper eyelid when the eyelid is closed and (b) the lower contact pad contacts a skin surface above the lower bone of the eye socket and below or on the lower eyelid when the eyelid is closed.

Left and right eyecup electrodes 200L and 200R are configured to optimize conductivity for more effective transfer of electrical energy, as described below. Left and right return electrodes 300L and 300R are placed in contact with a skin surface within each of left and right facial regions 430L and 430R, respectively, and close the return path for the treatment current back to signal generator 100. The current path from the skin surface of left eye region 420L to the skin surface of left facial region 430L during the treatment of left eye 410L is shown in FIG. 1. Of course, it should be understood that a general current path from the skin surface of right eye region 420R to the skin surface of right facial region would similarly be created during the treatment of right eye 410R.

A. Headset Applicator

Figure 2A:
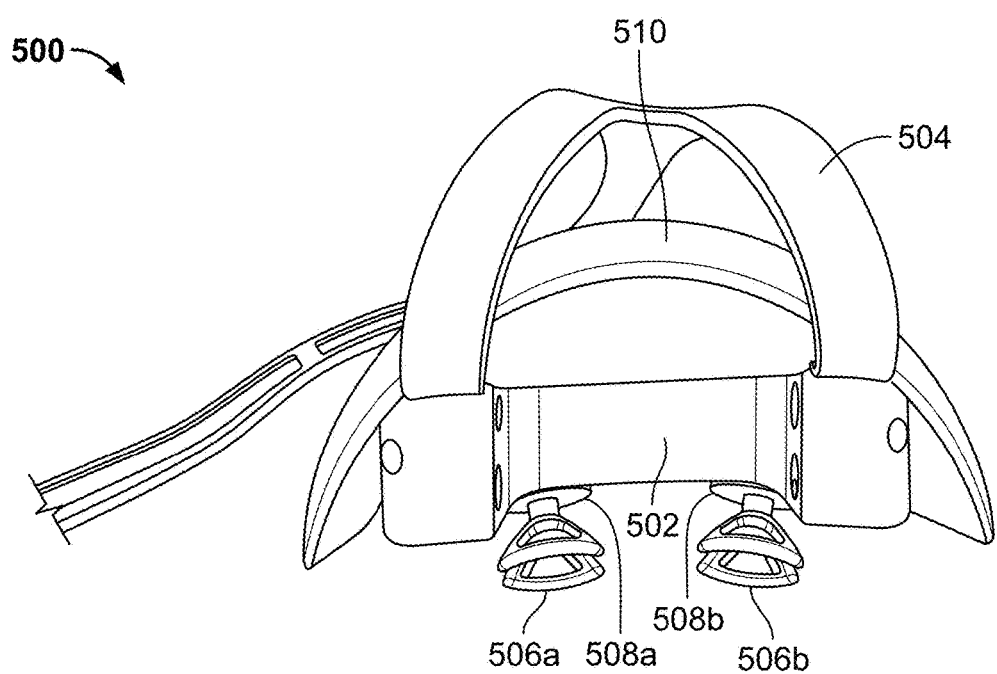
FIG. 2A is a top view of a headset in accordance with an exemplary embodiment of the present invention.
Figure 2B:
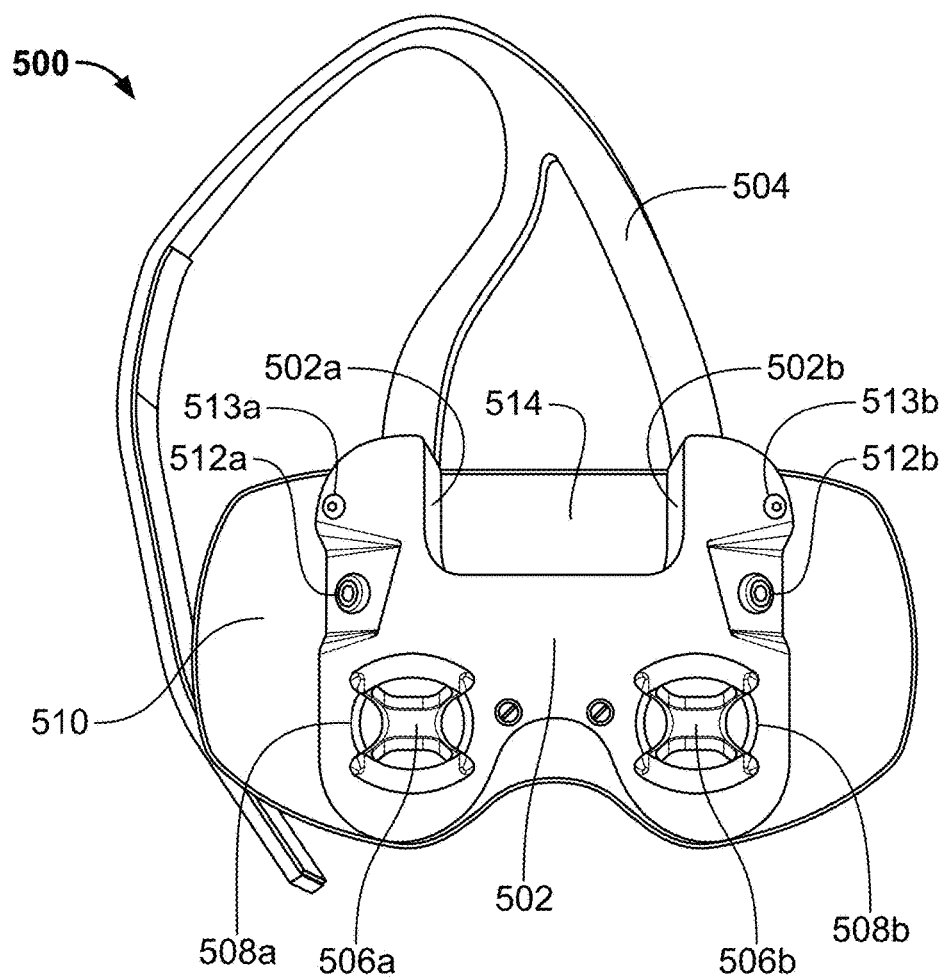
FIG. 2B is a rear view of the headset shown in FIG. 2A.
Figure 8A:
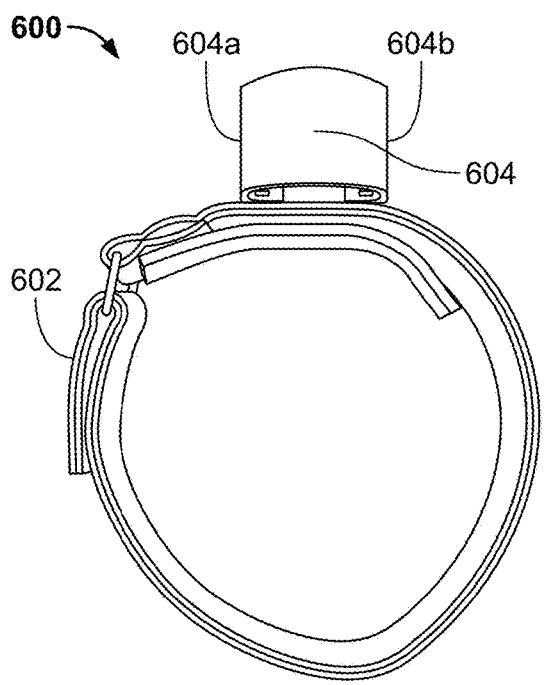
FIG. 8A is a top view of a headband in accordance with an exemplary embodiment of the present invention.
Figure 8B:
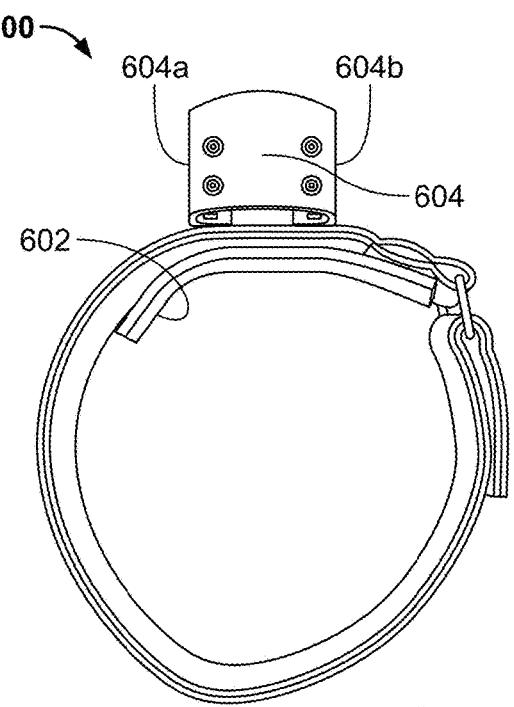
FIG. 8B is a bottom view of the headband shown in FIG. 8A.

The system of the present invention includes a headset applicator 200 that is comprised of a headset (an exemplary embodiment of which is shown in FIGS. 2A and 2B) that is mounted on a headband (an exemplary embodiment of which is shown in FIGS. 8A and 8B). Each of these components will be described in greater detail below.

With reference to FIGS. 2A and 2B, a headset in accordance with an exemplary embodiment of the present invention is shown as reference numeral 500. FIG. 2A shows the top view of headset 500 and FIG. 2B shows the rear view of headset 500 (i.e., the back side of the headset that faces the patient during use). Headset 500 includes a main housing 502 having a rigid structure that is configured to be mounted to a headband 600 (shown in FIGS. 8A and 8B), as described below. As best shown in FIG. 2B, the upper portion of main housing 302 has two attachments for supporting a Y-shaped strap assembly 504. Strap assembly 504 is configured to extend over the head of a patient and attach to the back of headband 600 using a hook and loop fastener (e.g., a Velcro® fastener) or any other type of attachment means. Preferably, the length of strap assembly 504 is adjustable to account for differences in the head sizes of different patients.

Headset 500 also includes a left eyecup electrode 506a and a right eyecup electrode 506b, which are the only components of headset 500 that are electrically connected to the patient's skin. Left and right eyecup electrodes 506a and 506b include mounting posts (described below with reference to the eyecup electrode shown in FIGS. 3A-3D) that are attached to left and right bellows 508a and 508b, respectively, which are positioned within corresponding recesses formed within main housing 502. Bellows 508a and 508b are designed with pressure fittings to allow left and right eyecup electrodes 506a and 506b to be changed out with eyecup electrodes of different sizes. Bellows 508a and 508b each comprise a spring component that is flexible and pliable to allow for up/down and left/right adjustments of the eyecup electrodes 506a and 506b, respectively, to account for small differences between the eye locations of different patients. A fascia 510 is also provided to cover the front of main housing 502.

As shown in FIG. 2B, two input cable connectors 512a and 512b are located on the back side of main housing 502. Input cable connectors 512a and 512b have identical functionality and, as such, either of these connectors can be used for connection to a signal generator via a cable or any other type of electrical connection means. It should be understood that only one of input cable connectors 512a and 512b is used at any one time depending on the preference of the patient and/or practitioner. Each of input cable connectors 512a and 512b is electrically connected to both of left and right eyecup electrodes 506a and 506b via wiring contained within main housing 502. As such, left and right eyecup electrodes 506a and 506b deliver the waveform generated by the signal generator to the skin surface within the left and right eye regions, respectively, when headset 500 is positioned on the patient.

Two return electrode connectors 513a and 513b are also located on the back side of main housing 502. Connector 513a is used for connection to a left return electrode located on a skin surface of the patient and connector 513b is used for connection to a right return electrode located on a skin surface of the patient. The left and right return electrodes are preferably placed near the left and right eyes, respectively, to reduce the length of the current path between each eyecup electrode and associated return electrode. In the exemplary embodiment, the left return electrode is placed on the patient's facial skin at or near the left temple and the right return electrode is placed on the patient's facial skin at or near the right temple. The return electrodes may comprise any type of contact electrodes known in the art, such as the Red Dot™ electrodes available from 3M™.

Referring still to FIG. 2B, main housing 502 includes a magnetic slot 514 configured to be mounted to a magnetic mount 604 positioned on the front of headband 600 (shown in FIGS. 8A and 8B). Magnetic slot 514 is defined by sidewalls 502a, 502b and 502c of main housing 502, and magnets located within main housing 502 along each of side walls 502a and 502b line up with opposite polarity magnets built into the sides of magnetic mount 604. The attractive forces of these magnets are strong enough to provide a frictional attachment between headset 500 and magnetic mount 604, yet allow for movement of headset 500 with respect to magnetic mount 604. As such, headset 500 can be mounted on magnetic mount 604 and gently rotated in a downward direction until left and right eyecup electrodes 506a and 506b contact the skin surface within the left and right eye regions, respectively.

In the exemplary embodiment, left and right eyecup electrodes 506a and 506b of headset 500 have the same configuration and, as such, only one eyecup will described in detail below with reference to the exemplary embodiment of FIGS. 3A-3D and the alternative embodiments of FIGS. 5A-5D, FIGS. 6A-6B and FIGS. 7A-7B.

In general terms, the eyecup electrode of the present invention may be configured in any manner that enables one or more contact pads to be spaced away from the main housing of the headset so as to enable contact with a skin surface within an eye region of a patient.

FIGS. 2A-2D shows various illustrations of the eyecup electrode used in headset 500. As can be seen, the eyecup is comprised of a center mounting post 520, an upper cup section 522, and a lower cup section 524 that are integrally formed as a single component. Of course, mounting post 520, upper cup section 522, and lower cup section 524 may be formed as separate components and connected together via any suitable means. In this embodiment, the eyecup electrode is made from medical grade stainless steel and is preferably electropolished in order to provide a smooth surface that is easier to sterilize. Of course, the eyecup electrode could also be made from a variety of different metals or other conductive materials.

Upper cup section 522 includes an upper contact pad 526 comprising an arc that curves concave downward that is spaced away from mounting post 520 so as to enable contact with a skin surface within an eye region. In this embodiment, the spacing between mounting post 520 and upper contact pad 526 is achieved through the use of two extension arms 528a and 528b that extend outwardly and upwardly from mounting post 520 and terminate at upper contact pad 526. Similarly, lower cup section 524 includes a lower contact pad 530 comprising an arc that curves concave upward that is spaced away from mounting post 520 so as to enable contact with a skin surface within an eye region. In this embodiment, the spacing between mounting post 520 and lower contact pad 530 is achieved through the use of two extension arms 532a and 532b that extend outwardly and downwardly from mounting post 520 and terminate at lower contact pad 530.

Figure 4:
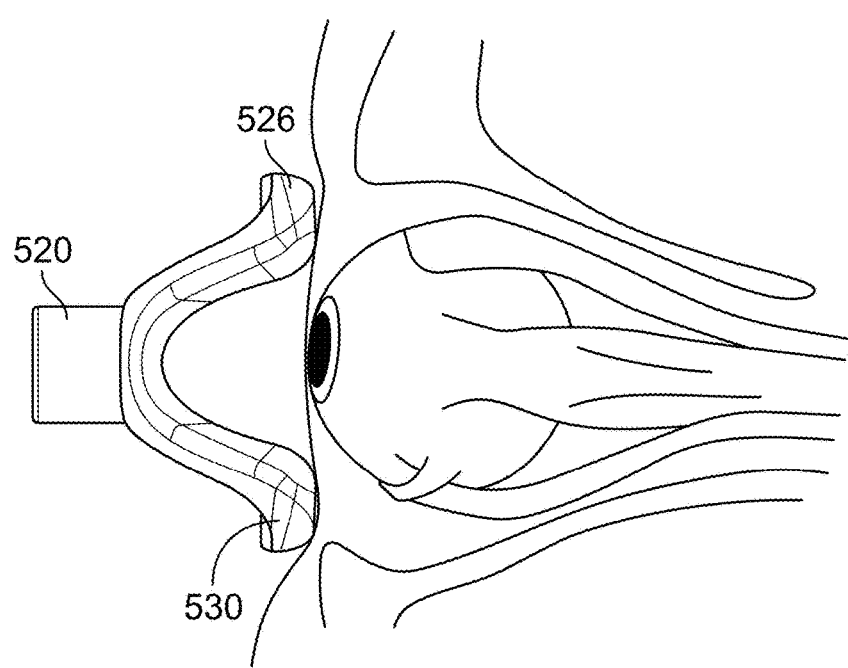
FIG. 4 is a side view of the eyecup electrode shown in FIGS. 3A-3D positioned in contact with a skin surface within a left eye region.
Figure 5A:
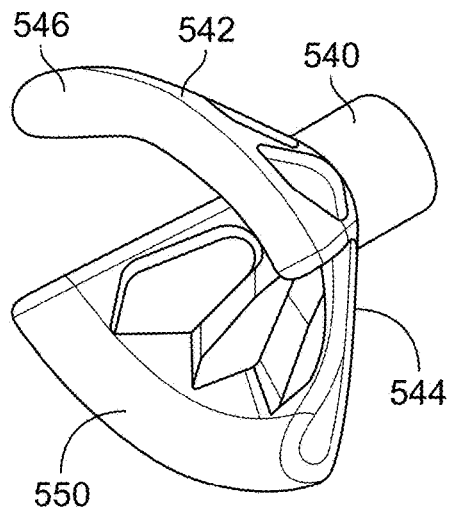
FIG. 5A is a perspective view of an eyecup electrode in accordance with a first alternative embodiment.
Figure 5B:
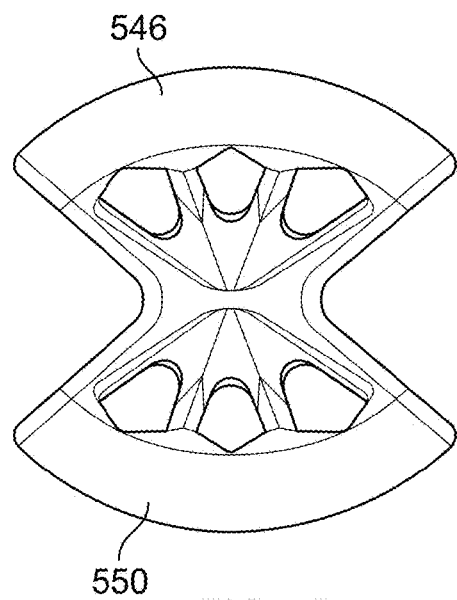
FIGS. 5B-5D are front, rear and side views of the eyecup electrode shown in FIG. 5A.
Figure 5C:
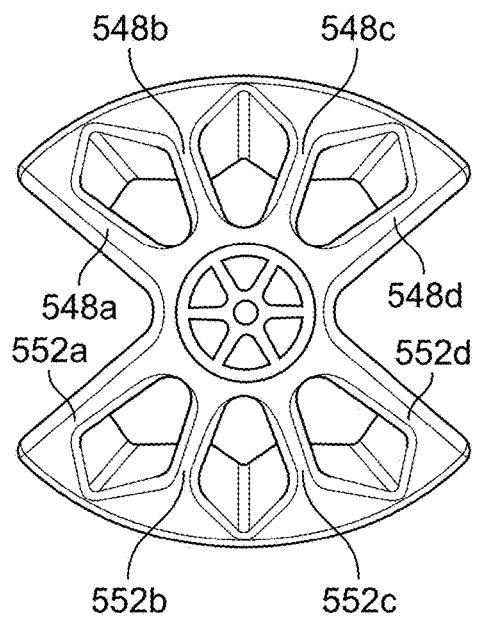
Figure 5D:
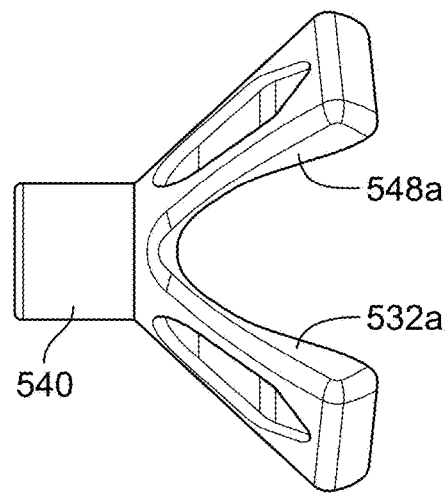

Upper and lower contact pads 526 and 530 are curved to fit within the ocular orbit such that (a) upper contact pad 526 contacts a skin surface located below the upper bone of the eye socket and above the upper eyelid when the eyelid is closed and (b) lower contact pad 530 contacts a skin surface above the lower bone of the eye socket and below or on the lower eyelid when the eyelid is closed, as shown in FIG. 4. Upper and lower contact pads 526 and 530 should not encroach on the area in front of the pupil of the eye and should not overlap with the bone of the eye socket. It can be appreciated that this configuration enables consistent and repeatable placement of upper and lower contact pads 526 and 530 on the skin surface within the eye region.

Eyecup electrodes 506a and 506b are configured to accommodate a variety of different eye shapes and sizes and different distances between the left and right eyes of different patients. The ability to use the same eyecup electrodes with different patients is possible due to the configuration of upper and lower contact pads 526 and 530. It is believed that eyecup electrodes 506a and 506b may be used on approximately 90% of the patient population. By contrast, if the contact pads of the eyecup electrodes were designed to fully encircle the eyes (such as the eyecup configuration shown in FIGS. 7A and 7B, discussed below), different eyecup sizes would be needed to accommodate different patients.

Of course, it should be understood that the present invention is not limited to the eyecup electrode configuration shown in FIGS. 3A-3D and that other eyecup electrode configurations may be used in accordance with the present invention, some examples of which are described below.

For example, FIGS. 5A-5D show various illustrations of an eyecup electrode that could be used with headset 500 in accordance with a first alternative embodiment. As can be seen, this eyecup electrode is comprised of a center mounting post 540, an upper cup section 542, and a lower cup section 544, which are either integrally formed as a single component or formed as separate components and connected together via any suitable means. Like the eyecup electrode described above, this eyecup electrode is made from medical grade stainless steel and is preferably electropolished in order to provide a smooth surface that is easier to sterilize.

Upper cup section 542 includes an upper contact pad 546 that is spaced away from mounting post 540 so as to enable contact with a skin surface within an eye region. In this embodiment, the spacing between mounting post 540 and upper contact pad 546 is achieved through the use of four extension arms 548a-548d that extend outwardly and upwardly from mounting post 540 and terminate at upper contact pad 546. Similarly, lower cup section 544 includes a lower contact pad 550 that is spaced away from mounting post 540 so as to enable contact with a skin surface within an eye region. In this embodiment, the spacing between mounting post 540 and lower contact pad 550 is achieved through the use of four extension arms 552a-552d that extend outwardly and downwardly from mounting post 540 and terminate at lower contact pad 550.

It can be appreciated that the only difference between the eyecup electrode shown in FIGS. 5A-5D and the eyecup electrode shown in FIGS. 3A-3D is that the number of extension arms has been increased from two extension arms to four extension arms. The configuration of the eyecup electrode shown in FIGS. 3A-3D is preferred insofar as it is simpler to manufacture and also easier to clean after use. With that said, the eyecup electrode shown in FIGS. 5A-5D may be used within the scope of the present invention.

Figure 6A:
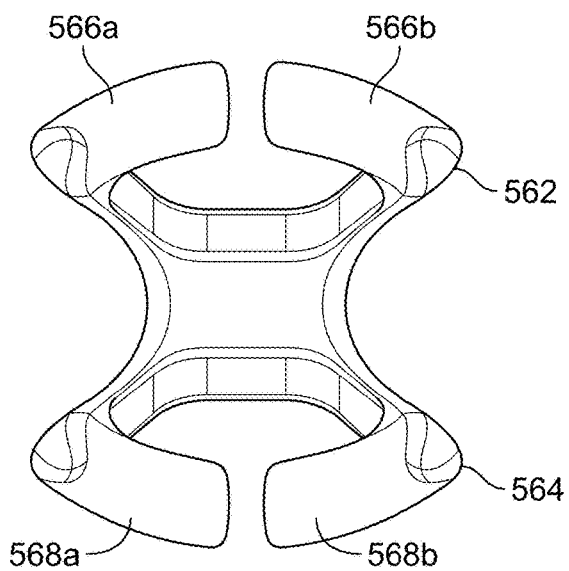
FIGS. 6A and 6B are front and side views of an eyecup electrode in accordance with a second alternative embodiment.
Figure 6B:
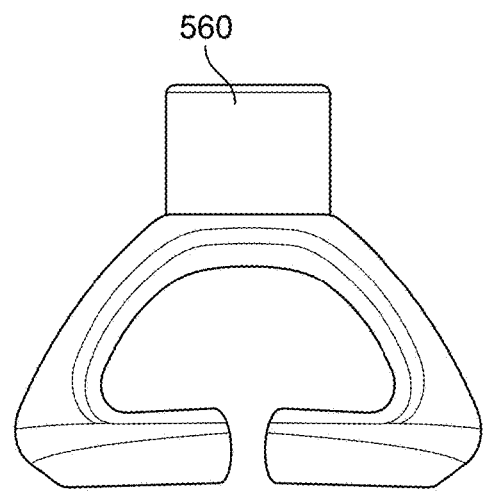

As another example, FIGS. 6A and 6B show various illustrations of an eyecup electrode that could be used in headset 500 in accordance with a second alternative embodiment. As can be seen, this eyecup electrode is comprised of a center mounting post 560, an upper cup section 562, and a lower cup section 564, which are either integrally formed as a single component or formed as separate components and connected together via any suitable means. Like the eyecup electrodes described above, this eyecup electrode is made from medical grade stainless steel and is preferably electropolished in order to provide a smooth surface that is easier to sterilize.

Upper cup section 562 includes two upper contact pad segments 566a and 566b that are separated from each other and spaced away from mounting post 560 so as to enable contact with a skin surface within an eye region. Similarly, lower cup section 564 includes two lower contact pad segments 568a and 568b that are separated from each other and spaced away from mounting post 560 so as to enable contact with a skin surface within an eye region. It can be appreciated that this multi-segmented eyecup electrode configuration is not preferred due to the difficulty of manufacturing the eyecup electrode and the reduced surface area of the contact pad segments compared to the contact pads shown in FIGS. 3A-3D and FIGS. 5A-5D. With that said, the eyecup electrode shown in FIGS. 6A and 6B may be used within the scope of the present invention.

Figure 7A:
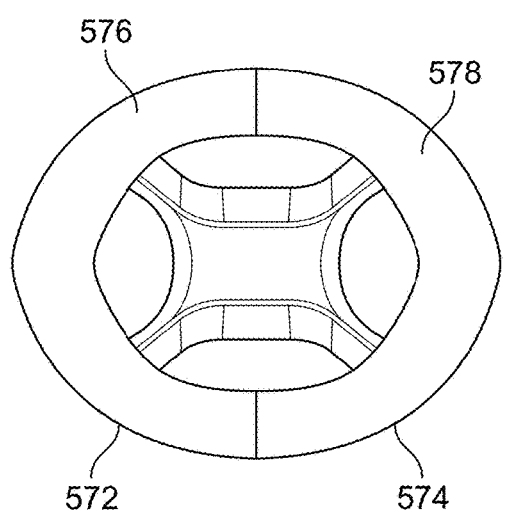
FIGS. 7A and 7B are front and side views of an eyecup electrode in accordance with a third alternative embodiment.
Figure 7B:
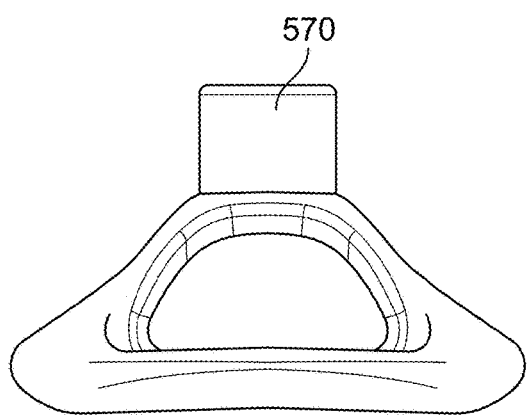

As yet another example, FIGS. 7A and 7B show various illustrations of an eyecup electrode that could be used in headset 500 in accordance with a third alternative embodiment. As can be seen, this eyecup electrode is comprised of a center mounting post 570, a left cup section 572, and a right cup section 574, which are either integrally formed as a single component or formed as separate components and connected together via any suitable means. Like the eyecup electrodes described above, this eyecup electrode is made from medical grade stainless steel and is preferably electropolished in order to provide a smooth surface that is easier to sterilize.

This eyecup electrode includes two contact pad segments 576 and 578 that are joined together to fully encircle the eye. This continuous contact pad is spaced away from mounting post 570 so as to enable contact with a skin surface within an eye region. It can be appreciated that this eyecup electrode configuration is not preferred because different eyecup sizes would be needed to accommodate different patients. With that said, the eyecup electrode shown in FIGS. 7A and 7B may be used within the scope of the present invention.

Other eyecup electrode configurations are also possible and within the scope of the present invention. For example, the upper and lower contact pads of the eyecup electrode shown in FIGS. 3A-3D could be connected to the mounting post via solid sidewalls (rather than the extension arms described above). However, the use of solid sidewalls is not preferred. Also, an eyecup electrode could be used in which the upper and lower contact pads are separately connected to the same current source or different current sources. However, this configuration is not effective electrically and would only be useful in applications that require treatment of the upper eye region without treatment of the lower eye region (or vice versa) or applications that require different waveforms to be applied to the upper and lower eye regions.

With reference to FIGS. 8A and 8B, a headband in accordance with an exemplary embodiment of the present invention is shown as reference numeral 600. FIG. 8A shows the top view of headband 600 and FIG. 8B shows the bottom view of headband 600. Headband 600 includes a single adjustment strap 602 that wraps around the circumference of the head of a patient and is closed using a hook and loop fastener (e.g., a Velcro® fastener) or any other type of attachment means. Preferably, the length of strap 602 is adjustable to account for differences in the head sizes of different patients. A forehead cushion may be secured to the inside of strap 602 at the front of headband 600 so as to provide cushioning when headband 600 and headset 500 are positioned on the patient's head.

Headband 600 also includes a magnetic mount 604 positioned on the front of headband 600 that is configured to receive magnetic slot 514 of headset 500 (see FIG. 2B). Magnets are built into the sides 604a and 604b of magnetic mount 604, and these magnets line up with opposite polarity magnets located within main housing 502 along each of side walls 502a and 502b. As discussed above, the attractive forces of these magnets are strong enough to provide a frictional attachment between headset 500 and magnetic mount 604, yet allow for movement of headset 500 with respect to magnetic mount 604. As such, headset 500 can be mounted on magnetic mount 604 and gently rotated in a downward direction until left and right eyecup electrodes 506a and 506b contact a skin surface within the left and right eye regions, respectively. Accordingly, left and right eyecup electrodes 506a and 506b exert minimal pressure on the skin surface to reduce or eliminate the potential of physical injury to a patient.

Magnetic mount 604 provides a physically strong and stable platform for headset 500 in order to address the human fatigue factor and eliminate operator errors associated with the use of hand held contact probes. Also, the mounting of headset 500 on magnetic mount 604 enables an accurate and consistent positioning of eyecup contact electrodes 506a and 506b on the skin surface within the left and right eye regions, respectively, which provides an accurate and consistent application of the treatment waveform to a patient.

B. Signal Generator and Treatment Waveform

The system of the present invention also includes a signal generator configured to automatically generate at least one treatment waveform that is provided to headset 500 and delivered to a skin surface of the left and right eye regions of a patient via left and right eyecup electrodes 506a and 506b, respectively, whereby the waveform is returned to the headset via the left and right return electrodes, respectively. Thus, the system includes two electrical interfaces that are used to deliver the waveform to the patient. The first interface is the contact surface of the left or right eyecup electrodes (e.g., upper and lower contact pads 526 and 530 shown in FIGS. 3A-3D). It should be noted that the contact pads are the only components of headset 500 that are electrically connected to the patient's skin. The second interface is the left or right return electrodes. These interfaces provide the electrical connection to transfer the energy of the current pulses to the patient.

Preferably, the contact pads and the return electrodes are each coated with a conductive gel to improve conductivity by providing moisture to the skin. The use of the gel also normalizes the treatment by providing a more consistent conductivity across the patient population. In addition, the gel acts as a surface contact multiplier and a contact bridge from the electrode to the skin surface of the patient.

The treatment waveform is comprised of a plurality of pulse sequences that are applied to each of the left and right eyes regions of the patient. Each pulse sequence is comprised of a series of current pulses of low current (microamps) in specific waveform patterns and well-defined frequency ranges. The shape of each of the current pulses is generally rectangular, although other pulse shapes may also be used in accordance with the present invention.

Figure 9:
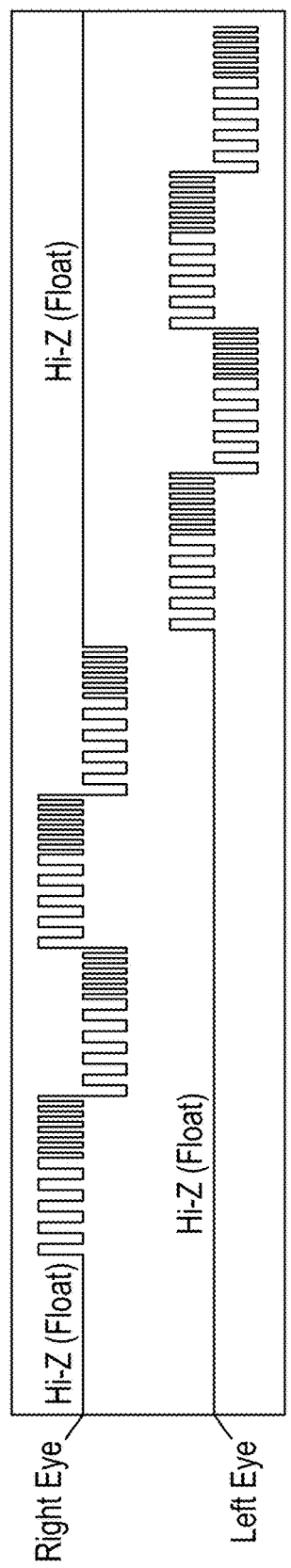
FIG. 9 illustrates a pulse sequence of an exemplary waveform delivered sequentially to a skin surface within the left and right eye regions of a patient via the headset shown in FIGS. 2A and 2B.

An exemplary treatment waveform that is believed to be therapeutically efficacious for treating age-related macular degeneration is shown in FIG. 9. As can be seen, the waveform comprises a bipolar constant peak current waveform that is comprised of a first pulse sequence applied to the right eye followed by a second pulse sequence applied to the left eye. During treatment, the eyecup electrode of the eye under treatment receives the pulse sequence, while the eyecup electrode of the untreated eye is held in a high impedance (HiZ) state, i.e., essentially an open circuit, during a resting period that allows the cells to return to a normalized electrical state. The first and second pulse sequences are repeated a desired number of times during a treatment session. In the exemplary embodiment, the duration of each pulse sequence is 40 seconds. Thus, if the first and second pulse sequences are repeated eight times, the total treatment time would be 640 seconds or just over 10 minutes. Of course, other time durations could also be used in accordance with the present invention. In alternative embodiments, the pulse sequence is applied to only the right eye or only the left eye, in which case the untreated eye would be held in a HiZ state during the entire treatment session.

In the exemplary embodiment, each pulse sequence includes four different series of current pulses—each of which is referred to as a cycle—that alternate in polarity. The first cycle comprises a 10-second series of pulses having a positive polarity, the second cycle comprises a 10-second series of pulses having a negative polarity, the third cycle comprises a 10-second series of pulses having a positive polarity, and the fourth cycle comprises a 10-second series of pulses having a negative polarity. With the exception of polarity, the series of current pulses in each cycle are identical.

Figure 10:
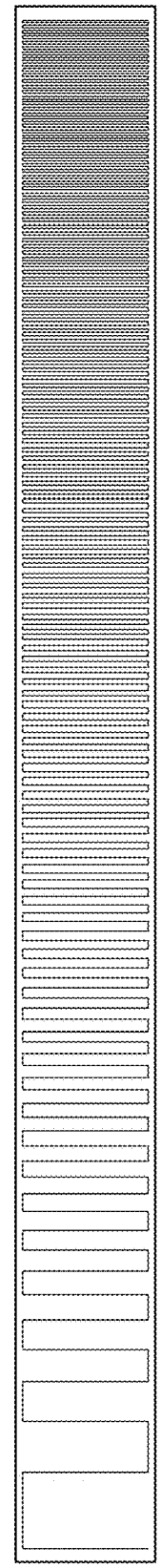
FIG. 10 illustrates one cycle of the pulse sequence shown in FIG. 9.

The series of current pulses in the first cycle is shown in greater detail in FIG. 10. As can be seen, the current pulses increase in frequency from a minimum frequency ($f_{min}$) to a maximum frequency ($f_{max}$) and the duty cycle is set at 50% during the treatment session. In the exemplary embodiment, the frequency ranges from 1 Hz to a maximum of 100 Hz. As such, each pulse can be analyzed as a small DC circuit. The boundary conditions for the voltage, current, resistance and frequency parameters of the exemplary embodiment are shown in Table 1 below:

TABLE 1

| Parameter | Minimum | Maximum | Typical |
|---|---|---|---|
| Voltage | 0 V | 23 V | 4 V |
| Current | 0 A | 200 uA | 160 uA |
| Resistance | 10 kOhms | 115 kOhms | 15 kOhms |
| Frequency | 1 Hz | 100 Hz | 50 Hz |

Of course, one skilled in the art will understand that other frequency ranges may also be provided in accordance with the present invention, such as 1 Hz to 30 Hz or 1 Hz to 50 Hz. Also, the duty cycle could vary in other embodiments.

Figure 11:
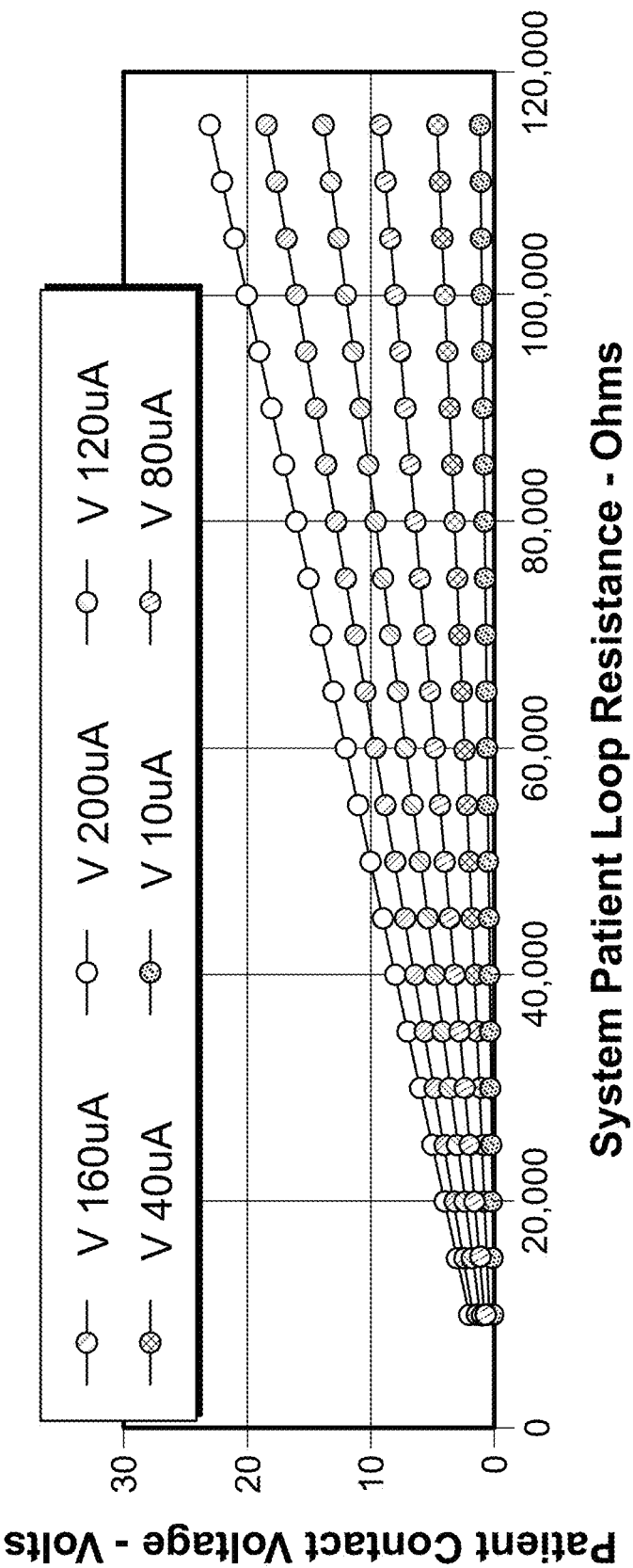
FIG. 11 is a plot showing the patient loop resistance in relation to the patient contact voltage for each of a plurality of pulse current levels.

It can be seen that the peak of each current pulse is substantially constant in the waveform shown in FIG. 10. The peak current amplitude is achieved by applying the correct voltage to the treatment pathway based on the resistance of the treatment path in accordance with Ohm's Law (i.e., I (current)=V (volts)/R (resistance)). The resistance of the treatment path is a function of the inherent resistivity of a material (e.g., human tissue) and the volume of material that the current passes through and, thus, the resistance differs between patients and will even change within the same patient during a treatment session. In order to compensate for the varying resistance, the voltage levels are dynamically adjusted during a treatment session to provide a substantially constant current. FIG. 11 is a plot that illustrates the resistance of the treatment path (in ohms) in relation to the contact voltage (in volts) for each of a plurality of current levels (i.e., 10, 40, 80, 120, 160 and 200 microamps).

In the exemplary embodiment, the maximum settable peak current amplitude is 200 microamps. It should be understood that the actual peak current amplitude may momentarily reach up to 240 microamps when the skin resistance fluctuates and for the time it takes for the current/voltage feedback measurements to be processed and adjusted, which typically would not exceed 50 milliseconds. Preferably, the signal generator includes a safety circuit that prevents the peak current amplitude from exceeding 300 microamps.

The exemplary waveform described above is believed to be therapeutically efficacious for treating age-related macular degeneration, resulting in an improved visual acuity, macular contrast and macular sensitivity. Of course, it should be understood that the present invention is not limited to the delivery of this exemplary waveform and a signal generator may be used to generate other waveforms with different waveform parameters. In general terms, the waveform parameters are preferably chosen so that the waveform is therapeutically efficacious for the specific visual disease being treated and the specific biochemical events, processes, and mechanisms-of-action to be influenced. As such, a variety of different waveforms may be delivered within the scope of the present invention.

II. Power and Energy Calculations

Figure 12:
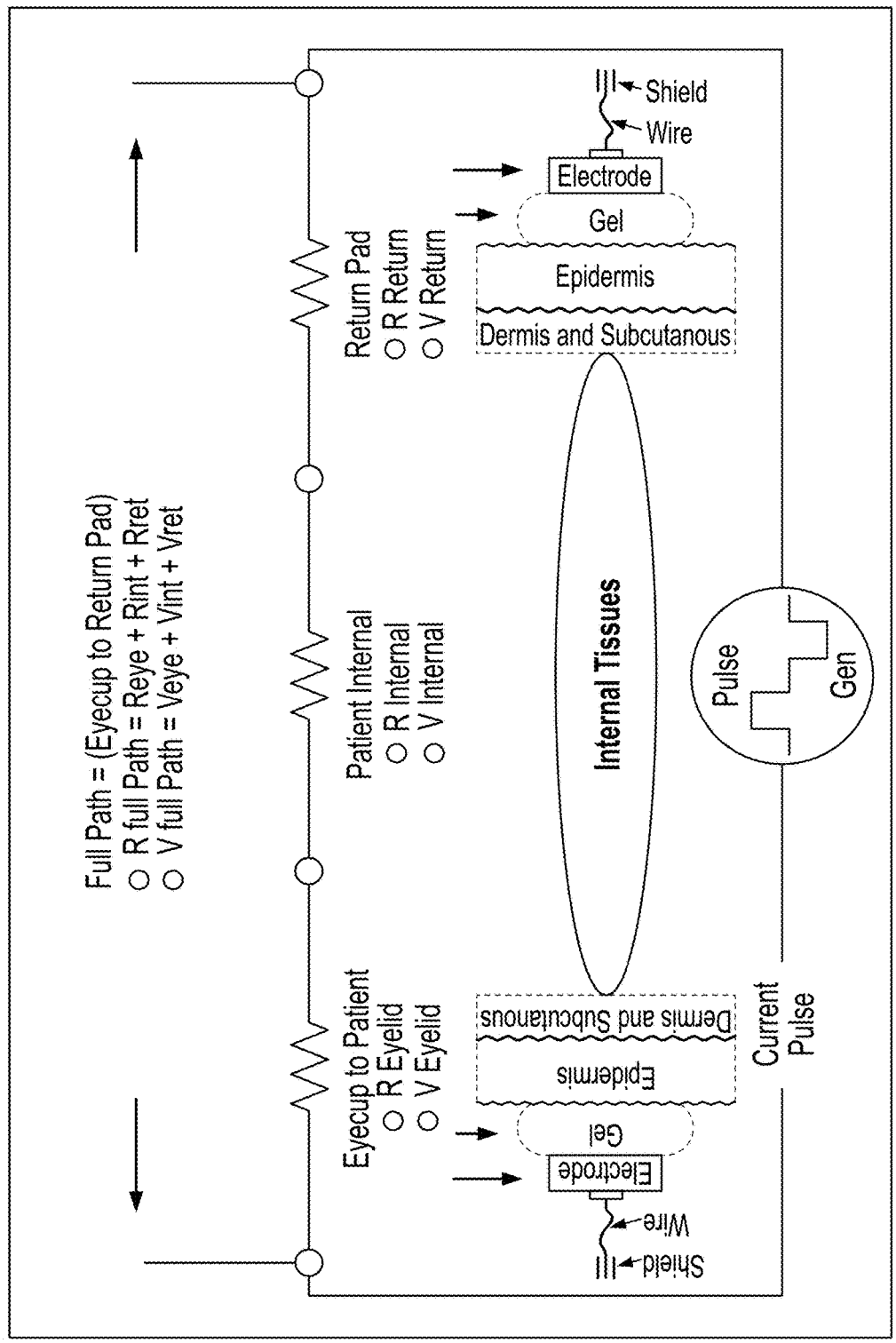
FIG. 12 is a diagram of a patient treatment path model showing the full path from an eyecup electrode to a return electrode.

FIG. 12 shows a patient treatment path model for a single eye under treatment and illustrates the flow of current from the eyecup electrode to the return electrode through the bio-conductive tissues located therebetween. As can be seen, the model comprises a simple three-resistor series circuit in which each resistor represents one of three zones of tissue and electrode resistance. The resistor of the first zone represents the eyecup electrode to subcutaneous skin layer resistance, the resistor of the second zone represents the internal cranial path resistance, and the resistor of the third zone represents the return electrode to subcutaneous skin layer resistance. Each of these zones will be described in greater detail below, wherein the subscripts 1, 2 and 3 will be used to refer to values associated with the first, second and third zones, respectively.

Figure 13:
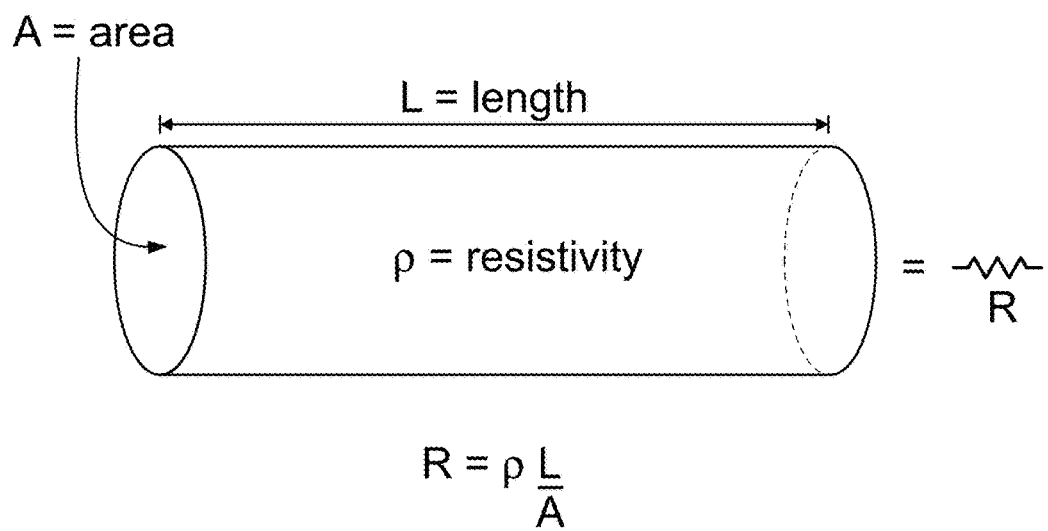
FIG. 13 is a diagram showing the calculation of resistance for a volume of material.

With reference to FIG. 13, it should be understood that all material has an intrinsic resistivity property called rho ($\rho$), which is a measure of the material's ability to conduct electricity. The resistance of a material is dependent, in part, on this resistivity and can be calculated from the following equation:

$$R = \rho \times L/A \qquad (1)$$

where:
R=resistance of material in ohms;
$\rho$=resistivity of material in ohm-meters;
L=length of material in meters; and
A=cross-sectional area of material in meters$^2$.

Based on equation (1), it can be appreciated that longer treatment paths have more resistance and wider treatment paths have less resistance.

Figure 14:
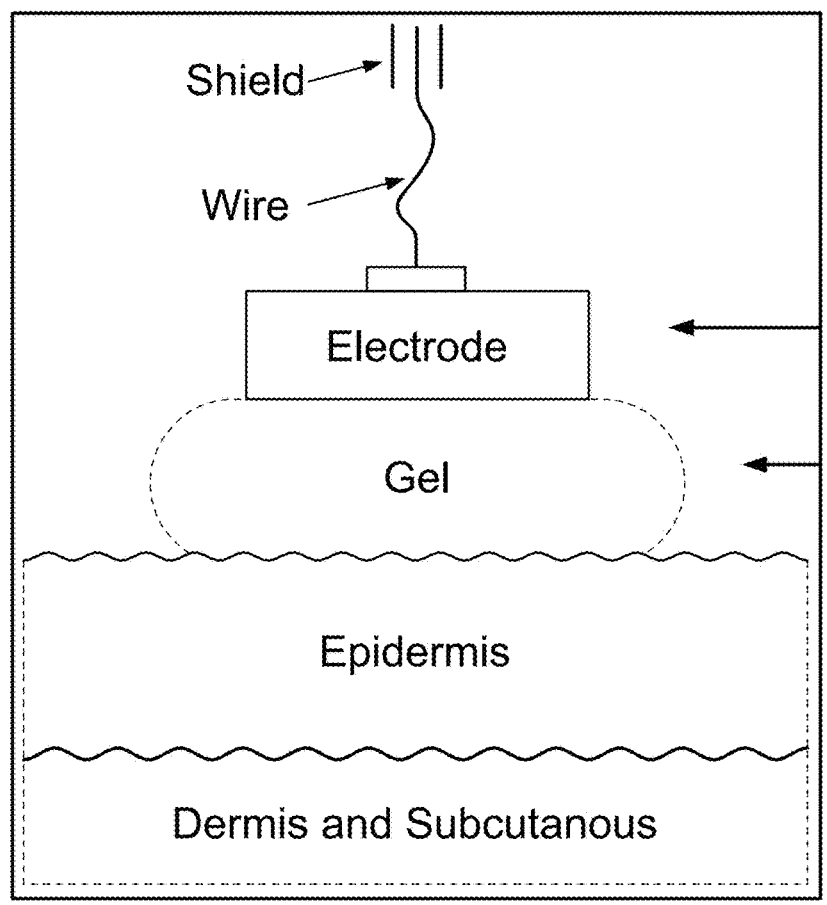
FIG. 14 is a diagram of an electrode (either an eyecup electrode or a return electrode) that is coated with a gel and placed in contact with a skin surface within an eye region.

Referring again to FIG. 12, the resistor of the first zone represents the eyecup electrode to subcutaneous skin layer resistance. FIG. 14 shows the stack of layers associated with the first zone, including the eyecup electrode, the gel applied to the electrode, the epidermis layer, and the dermis and subcutaneous layers. With reference to equation (1), it should be understood that A is the contact surface area of the eyecup electrode and L is the thickness of the eyelid skin between the eyecup electrode and the bottom subcutaneous layer. We will assume that the thickness of the eyelid skin is 0.06 cm in this example.

Figure 3A:
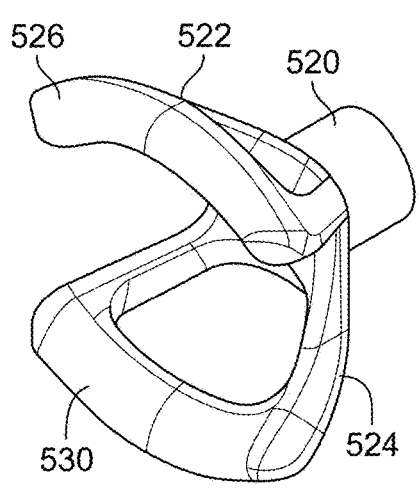
FIG. 3A is a perspective view of the eyecup electrode used in the headset shown in FIGS. 2A and 2B, and FIGS. 3B-3D are front, rear and side views of the eyecup electrode shown in FIG. 3A.
Figure 3B:
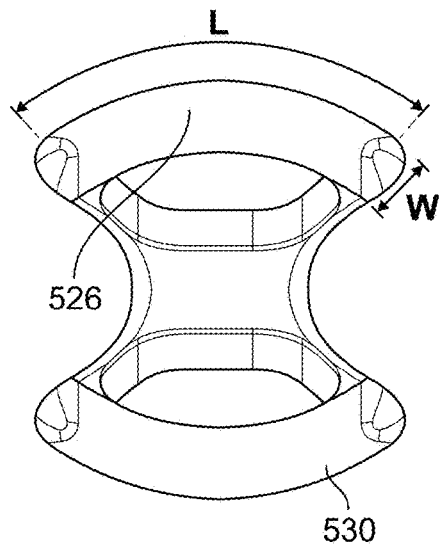
Figure 3C:
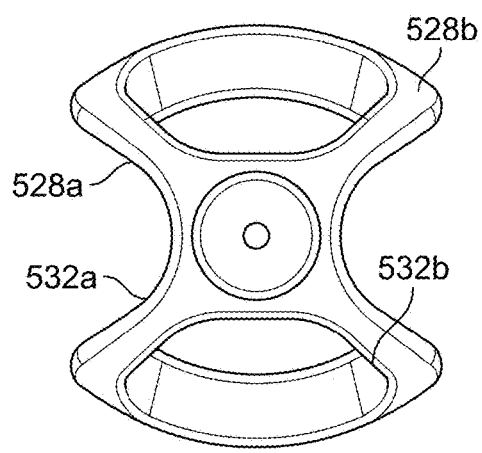
Figure 3D:
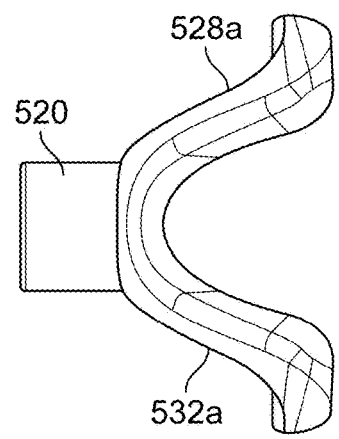

The eyecup electrode is configured to minimize the resistance of the first resistor shown in FIG. 12 by maximizing the contact surface area A. The contact surface (e.g., the surface of the upper and lower contact pads) of the eyecup electrode has a contact surface area that is greater than the contact surface area of a hand held contact probe or the individual contacts of a goggles-type device or eyeglass frame-type device. Preferably, the contact surface area of the eyecup electrode is in the range of about 1.10 cm$^2$ to about 1.80 cm$^2$ (or any range therebetween). In the eyecup electrode of the exemplary embodiment, each of the contact pads has a length (L) of 2.25 cm and a width (W) of 0.33 cm, as shown in FIG. 3B. Thus, the contact surface area of each contact pad is 2.25 cm×0.33 cm=0.7425 cm$^2$ and the total contact surface area is 1.49 cm$^2$. The use of contacts pads with a higher contact surface area reduces the total skin resistance, which enables less total voltage to be applied to the patient in order to achieve the same target current.

Still referring to FIG. 12, the resistor of the second zone represents the internal cranial path resistance. This resistance is difficult to calculate as the zone consists of different tissues, bone, vessels, etc. with different resistivity values. The length of the internal treatment path also affects the overall resistance. We will assume that the resistance of the internal cranial path is 300 to 1000 ohms, which is based on the assumption that (1) the resistivity of the cranium is homogenous and (2) the length of the internal treatment path is 3 to 5 cm. We will use the highest resistance value of 1000 ohms (i.e., 1 kOhm) in this example.

Still referring to FIG. 12, the resistor of the third zone represents the return electrode to subcutaneous skin layer resistance. The layers shown in FIG. 14 also apply to the third zone, including the return electrode, the gel applied to the electrode, the epidermis layer, and the dermis and subcutaneous layers. With reference to equation (1), it should be understood that A is the contact surface area of the return electrode and L is the thickness of the facial skin between the return electrode and the bottom subcutaneous layer. We will assume that the thickness of the facial skin is 0.17 cm in this example.

Preferably, the contact surface area of the return electrode is in the range of about 2.0 cm$^2$ to about 4.0 cm$^2$ (or any range therebetween). In this example, each of the return electrodes has a diameter of 2 cm or a radius of 1 cm. Thus, the contact surface area of each return electrode is $\pi \times (1 \text{ cm})^2 = 3.14 \text{ cm}^2$.

It should be understood that the two skin interfaces (i.e. the first and third zones shown in FIG. 12) have the largest resistances and, thus, represent the largest voltage drops and power dissipation along the current path. Compared to the internal cranial path resistance of 300 to 1000 ohms, the resistance of each of these skin interfaces can be orders of magnitude higher, e.g., a resistance of 12,000 ohms is frequently measured for each skin interface.

Using equation (1), the ratio of the resistance of the first zone to the resistance of the third zone can be expressed as follows:

$$\text{Ratio} = R_1/R_3 = (\rho_1 \times L_1/A_1)/(\rho_3 \times L_3/A_3) \quad (2)$$

where:
Ratio=resistance ratio of first zone to third zone;
$R_1$=resistance of first zone in ohms;
$R_3$=resistance of third zone in ohms;
$\rho_1$=resistivity of eyelid skin in ohm-meters;
$L_1$=thickness of eyelid skin in meters;
$A_1$=cross-sectional area of eyecup electrode in meters$^2$;
$\rho_3$=resistivity of facial skin in ohm-meters;
$L_3$=thickness of facial skin in meters; and
$A_3$=cross-sectional area of return electrode in meters$^2$.

Assuming that the skin resistivity ($\rho$) for the eyelid skin is similar to that for the facial skin, the relative skin thicknesses and contact surface areas of the eyecup electrode and return electrode will dominate how much resistance is seen by the signal generator at the skin interfaces. As such, the resistance ratio of equation (2) can be simplified as follows:

$$\text{Ratio} = R_1/R_3 = (L_1/A_1)/(L_3/A_3) \quad (3)$$

Assuming that $L_1$ is 0.6 cm (the thickness of the eyelid skin), $A_1$ is 3.14 cm$^2$ (the contact surface area of the eyecup electrode), $L_3$ is 0.17 cm (the thickness of the facial skin), and $A_3$ is 3.14 cm$^2$ (the contact surface area of the return electrode), the resistance ratio can be calculated using equation (3) as follows:

$$\text{Ratio} = R_1/R_3 = (0.06/3.14)/(0.17/1.49) = 0.743 \quad (4)$$

Equation (4) can be solved for $R_1$ and rewritten as follows:

$$R_1 = R_3 \times 0.743 \quad (5)$$

The total resistance ($R_{total}$) of the treatment path is the sum of the resistances of the first zone ($R_1$), the second zone ($R_2$) and the third zone ($R_3$), as follows:

$$R_{total} = R_1 + R_2 + R_3 \quad (6)$$

Assuming that the total resistance ($R_{total}$) is 25 kOhms and the resistance of the second zone ($R_2$) is 1 kOhm, equation (6) can be rewritten as follows:

$$R_1 = 25 \text{ kOhms} - 1 \text{ kOhm} - R_3 = 24 \text{kOhms} - R_3 \quad (7)$$

Equations (5) and (7) can then be combined as follows:

$$R_3 \lambda 0.743 = 24 \text{ kOhms} - R_3 \quad (8)$$

Equation (8) can be solved for $R_3$ and rewritten as follows:

$$R_3 = 24 \text{ kOhms}/(1+0.743) = 13.70 \text{ kOhms} \quad (9)$$

With $R_3$ calculated to be 13.769 kOhms, equation (7) can be used to calculate $R_1$ as follows:

$$R_1 = 24 \text{ kOhms} - 13.769 \text{ kOhms} = 10.23 \text{ kOhms} \quad (10)$$

For this example, Table 2 below summarizes various parameters associated with zone 1, zone 2, zone 3, and the total treatment path, including the contact surface area of each zone (set forth above), the thickness of each zone (set forth above), the volume of each zone (calculated as area×thickness), the resistance of each zone (calculated above), and the voltage drop across each zone (calculated as current×resistance, assuming a target current of 160 microamps):

TABLE 2

| Tissue Region | Area (cm$^2$) | Thickness (cm) | Volume (cm$^3$) | Resistance (kOhms) | Voltage Drop (volts) |
|---|---|---|---|---|---|
| Zone 1 | 1.49 | 0.06 | 0.089 cm$^3$ | 10.23 | 1.63 |
| Zone 2 | Unmappable | 2.0 to 5.0 (Patient Dependent) | Estimated Volume | 1 | 0.16 |
| Zone 3 | 3.14 | 0.17 | 0.534 cm$^3$ | 13.70 | 2.19 |
| Total Treatment Path | Unmappable | Total Path | Estimated Volume | 25 | 4.00 |

Power distribution and dissipation is important for both effective treatment and patient safety. The peak power that is dissipated within the tissues along the treatment path is provided by the following equation:

$$P_{peak} = I_{peak}^2 \times R \quad (11)$$

where:
$P_{peak}$=peak power dissipated within tissues in watts;
$I_{peak}$=peak current amplitude in amps; and
R=resistance of tissues in ohms.

The average treatment power can be calculated by multiplying the peak current amplitude by (1) the ratio of the pulse "on" time during a pulse cycle to the total cycle time (i.e., the duty cycle of the waveform) and (2) the ratio of the cycle "on" time during a pulse sequence to the total pulse sequence time. For example, in the exemplary embodiment, the pulses shown in FIG. 10 are "on" for 50% of the total cycle time (i.e., the duty cycle of the waveform is 50%) and the cycles shown in FIG. 9 are "on" for 50% of the total pulse sequence time due to the alternate eye resting periods. Thus, the average treatment power can be expressed as follows:

$$P_{avg} = P_{peak} \times 50\% \times 50\% = P_{peak} \times 25\% \quad (12)$$

The treatment energy may be expressed by the following equation:

$$E = P_{avg} \times \Delta t \quad (13)$$

where:
E=treatment energy in Joules (or Watt-Seconds);
$P_{avg}$=average power dissipated within tissues in amps; and
$\Delta t$=treatment duration in seconds.

For this example, Table 3 below summarizes various parameters associated with zone 1, zone 2, zone 3, and the total treatment path, including the resistance of each zone (from Table 2), the voltage drop across each zone (from Table 2), the peak power (calculated using equation (11) above and assuming a target current of 160 microamps), the average power (calculated using equation (12) above), and the energy (calculated using equation (13) above and assuming that the treatment duration is 30 minutes or 1800 seconds):

TABLE 3

| Tissue Region | Resistance (kOhms) | Voltage Drop (volts) | Peak and Average Power (uW) | Energy (mJ) |
|---|---|---|---|---|
| Zone 1 | 10.23 | 1.63 | 262 ($P_{peak}$)<br>65 ($P_{avg}$) | 118 |
| Zone 2 | 1.00 | 0.16 | 26 ($P_{peak}$)<br>6.4 ($P_{avg}$) | 11.5 |
| Zone 3 | 13.70 | 2.19 | 353 ($P_{peak}$)<br>88 ($P_{avg}$) | 159 |
| Total Treatment Path | 25.00 | 4.00 | 640 ($P_{peak}$)<br>160 ($P_{avg}$) | 288 |

A number of observations may be made from Table 3 above, including: (1) the peak power for the total treatment path is 640 uW; (2) the average power for the total treatment path is 160 uW, which is ¼ of the peak power across the total treatment path due to the combined effects of waveform duty cycle and alternate eye resting periods; (3) the two skin interfaces dissipate 96% of the total treatment power and the residual 4% of the treatment power is dissipated within the internal cranial tissue; (4) the peak power for the internal cranial tissue is 26 uW per eye, which is well below the threshold known to cause tissue heating or irreversible electroporation and well below documented thresholds of neural activation; (5) the total energy applied during the 30-minute treatment is 576 mJ (i.e., 288 mJ/eye×2 eyes) and, thus, each patient receives slightly more than ½ Joule of total body energy during the treatment; (6) 96% of the total energy applied during the 30-minute treatment is absorbed crossing the skin interfaces and the internal cranial tissue absorbs less than 4% of the total energy; (7) the internal cranial energy is distributed across the cranial hemisphere due to the increased conductive nature of these tissues and, thus, there is much less concentration of energy in any specific tissue such as the retina or optic nerve; and (8) the increased surface area of each eyecup electrode results in an overall lower resistance and a measurable safety improvement due to the lower source voltage required to achieve the target current, which translates to less energy entering into the body to achieve a given result.

III. Method of Operation

The direct electrical stimulation delivery system of the present invention is used to provide microcurrent stimulation to treat patients suffering from a variety of different visual diseases, including age-related macular degeneration.

Figure 15A:
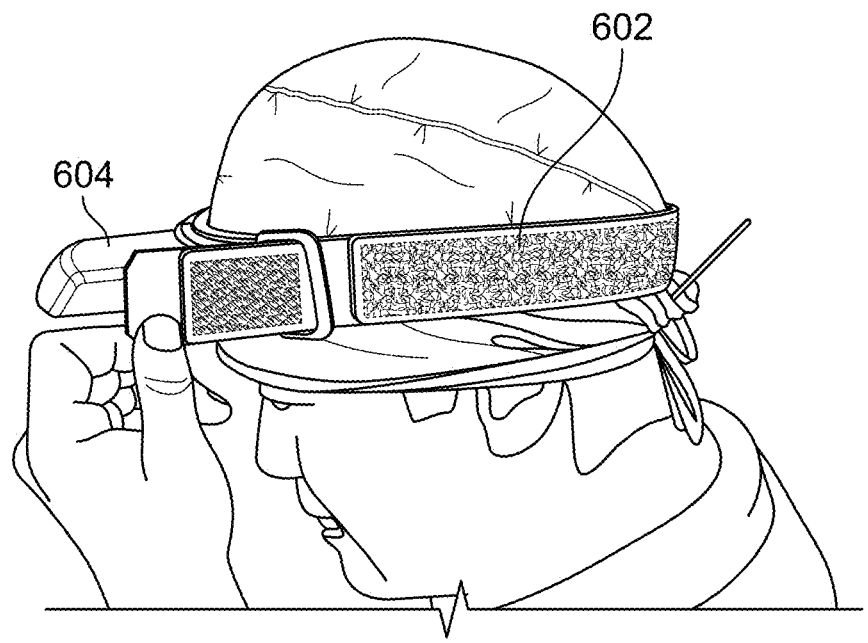
FIG. 15A illustrates the placement of the headband shown in FIGS. 8A and 8B on the head of a patient.
Figure 15B:
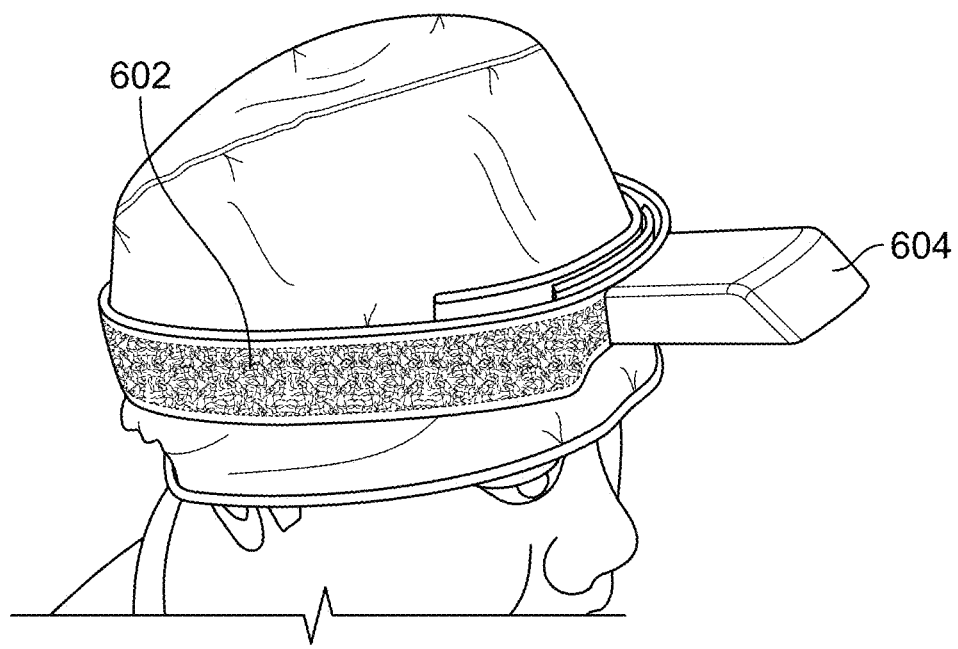
FIGS. 15B-15D illustrate various positions of the magnetic mount of the headband shown in FIG. 15A.
Figure 15C:
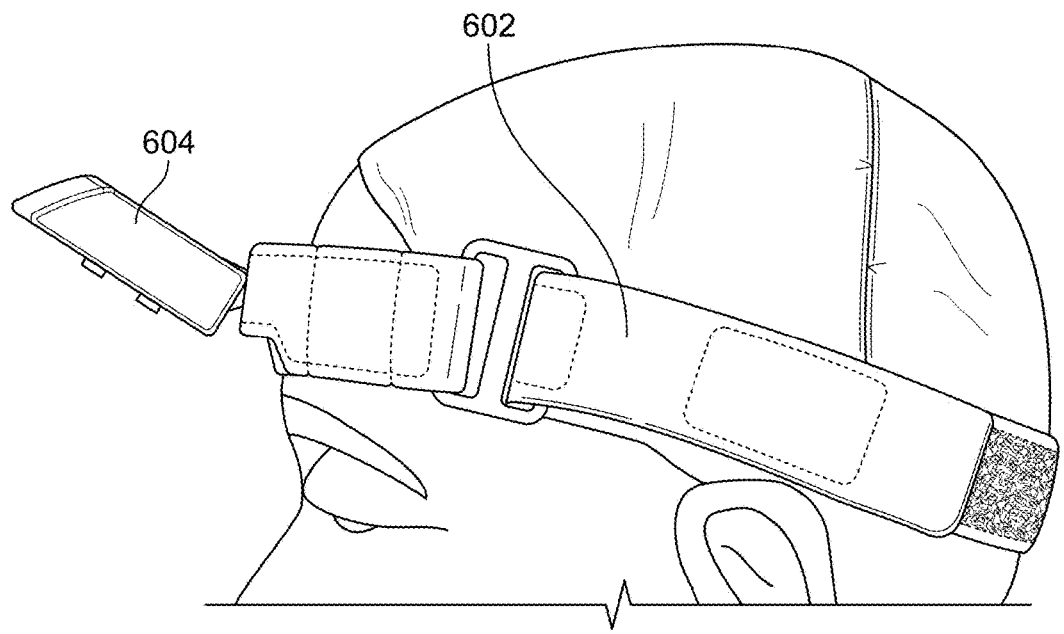
Figure 15D:
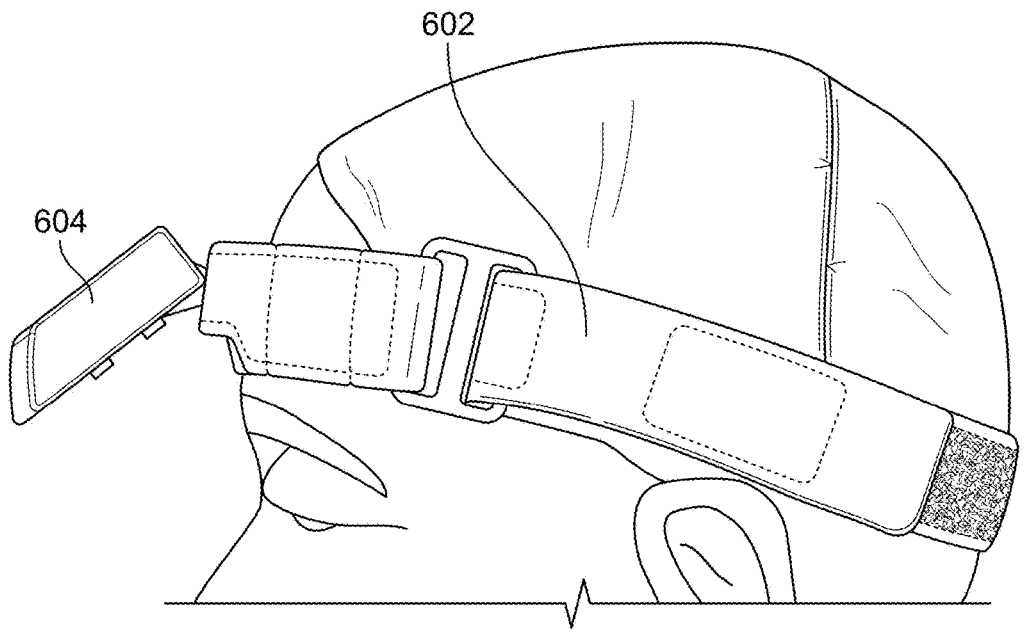

An exemplary method of using the electrical stimulation delivery system will now be described with reference to FIGS. 15A-15E. First, a disposable head cap is placed on a patient such that the cap does not cover the patient's eyelids or surrounding area. Next, headband 600 is placed on the patient's head over the disposal head cap and strap 602 is adjusted as shown in FIG. 15A so that headband 600 is snugly fitted to the head. If headband 600 is too loose, headset 500 will not stay in the proper position during treatment. FIG. 15B shows the proper placement of headband 600 on the patient's head. As shown in FIGS. 15C and 15D, magnetic mount 604 may be pivoted up and down in order to adjust its vertical height, as described below.

Next, a light coating of conductive gel is applied to the entire contact surface area of left and right eyecup electrodes 506a and 506b of headset 500 to ensure good electrical connectivity. Magnetic slot 514 of headset 500 is then placed over magnetic mount 604 of headband 600. In order to make a course adjustment of the position of headset 500, magnetic mount 604 is pivoted up or down as described above to center headset 500 around the patient's eyes. Strap assembly 504 is then pulled over the top of the patient's head and attached to the back of headband 600.

Figure 15E:
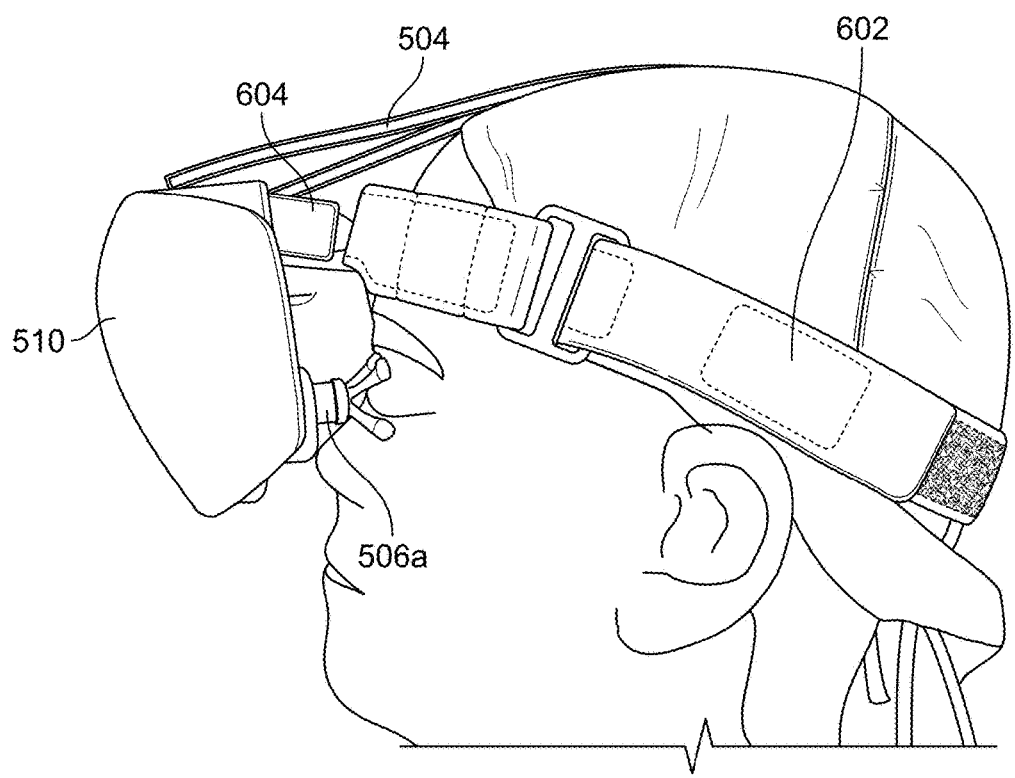
FIG. 15E illustrates the headset shown in FIGS. 2A and 2B mounted on the magnetic mount of the headband shown in FIG. 15A.

After attaching strap assembly 504 to the back of headband 600, it may be necessary to perform a fine adjustment of the position of headset 500 to ensure proper alignment of eyecup electrodes 506a and 506b and pressure to the skin surfaces within the left and right eye regions of the patient. To adjust the alignment, headset 500 may be moved up or down in relation to magnetic mount 604 in order to align left and right eyecup electrodes 506a and 506b with the patient's eyes. It is also possible to readjust the attachment of strap assembly 504 to the back of headband 600 to change the vertical position of headset 500. To adjust the pressure, headset 500 may be moved in or out in relation to magnetic mount 604 in order to adjust the pressure of left and right eyecup electrodes 506a and 506b to the skin surfaces within the left and right eye regions. The pressure should be very light and comfortable for the patient. FIG. 15E shows the proper placement of headset 500 on the patient's head.

Next, a signal generator is used to deliver a waveform (as described above) to right eyecup electrode 506b and then to left eyecup electrode 506a of headset 500, as applicable. A closed circuit is created when the eyecup electrode is placed in contact with the skin surface within the eye region and the return electrode is attached to the skin surface of the facial region (e.g., at or near the patient's temple). The waveform generated by the signal generator travels from the eyecup electrode through the patient's body to the return electrode and back to the headset. This process may be performed multiple times on both eyes during a treatment session. In one embodiment, the waveform is applied to the right eye for 40 seconds and then to the left eye for 40 seconds, and this process is repeated for a total of 30 minutes.

IV. General

The description set forth above provides several embodiments of the inventive subject matter. Although each embodiment represents a single combination of inventive elements, the inventive subject matter is considered to include all possible combinations of the disclosed elements. Thus, if one embodiment comprises elements A, B, and C, and a second embodiment comprises elements B and D, then the inventive subject matter is also considered to include other remaining combinations of A, B, C, or D, even if not explicitly disclosed.

The use of any and all examples or exemplary language (e.g., "such as") provided with respect to certain embodiments is intended merely to better describe the invention and does not pose a limitation on the scope of the invention. No language in the description should be construed as indicating any non-claimed element essential to the practice of the invention.

While the present invention has been described and illustrated hereinabove with reference to several exemplary embodiments, it should be understood that various modifications could be made to these embodiments without departing from the scope of the invention. Therefore, the present invention is not to be limited to the specific structural configurations or methodologies of the exemplary embodiments, except insofar as such limitations are included in the following claims.

The invention claimed is:

1. An electrotherapeutic system for treating a visual disease, comprising:
   a signal generator configured to generate a waveform comprising a series of current pulses; and
   a headset connectable to the signal generator and configured to deliver the waveform to a skin surface within an eye region of a patient, wherein the headset comprises at least one eyecup electrode including an upper contact pad and a lower contact pad having a contact surface with an area in a range of about 1.10 cm$^2$ to about 1.80 cm$^2$, wherein the eyecup electrode includes a mounting post and a plurality of upper extension arms that provide spacing between the mounting post and the upper contact pad and a plurality of lower extension arms that provide spacing between the mounting post and the lower contact pad to enable contact of the upper and lower contact pads with the skin surface, and wherein the waveform is delivered to the skin surface through both the upper and lower contact pads.

2. The electrotherapeutic system of claim 1, further comprising a headband having a magnetic mount, wherein the headset includes a magnetic slot configured to be mounted to the magnetic mount.

3. The electrotherapeutic system of claim 1, wherein the upper contact pad comprises an arc that curves concave downward and the lower contact pad comprises an arc that curves concave upward.

4. The electrotherapeutic system of claim 1, wherein the headset comprises a left eyecup electrode and a right eyecup electrode, wherein the contact surface of the left eyecup electrode is positioned for contact with a skin surface within a left eye region and the contact surface of the right eyecup electrode is positioned for contact with a skin surface within a right eye region.

5. The electrotherapeutic system of claim 4, wherein the left and right eyecup electrodes are the only components of the headset that are electrically connected to a skin surface of the patient.

6. The electrotherapeutic system of claim 4, further comprising a left return electrode and a right return electrode, wherein the left return electrode is connectable to complete a current path originating from the left eyecup electrode, wherein the right return electrode is connectable to complete a current path originating from the right eyecup electrode.

7. An electrotherapeutic system for treating a visual disease, comprising:
   a signal generator configured to generate a waveform comprising a series of current pulses; and
   a headset connectable to the signal generator and configured to deliver the waveform to a skin surface within an eye region of a patient, wherein the headset comprises at least one eyecup electrode having a contact surface comprising an upper contact pad and a lower contact pad, wherein the upper contact pad comprises an arc made from a conductive material that curves concave downward and is positioned for contact with an upper portion of the skin surface, and wherein the lower contact pad comprises an arc made from the conductive material that curves concave upward and is positioned for contact with a lower portion of the skin surface, and wherein the eyecup electrode includes a mounting post and a plurality of upper extension arms that provide spacing between the mounting post and the upper contact pad and a plurality of lower extension arms that provide spacing between the mounting post and the lower contact pad to enable contact of the upper and lower contact pads with the upper and lower portions of the skin surface, respectively.

8. The electrotherapeutic system of claim 7, further comprising a headband having a magnetic mount, wherein the headset includes a magnetic slot configured to be mounted to the magnetic mount.

9. The electrotherapeutic system of claim 7 wherein the upper contact pad and the lower contact pad have a total area in a range of about 1.10 cm$^2$ to about 1.80 cm$^2$.

10. The electrotherapeutic system of claim 7, wherein the headset comprises a left eyecup electrode and a right eyecup electrode, wherein the upper and lower contact pads of the left eyecup electrode are positioned for contact with the upper and lower portions of a skin surface within a left eye region, wherein the upper and lower contact pads of the right eyecup electrode are positioned for contact with the upper and lower portions of a skin surface within a right eye region.

11. The electrotherapeutic system of claim 10, wherein the left and right eyecup electrodes are the only components of the headset that are electrically connected to a skin surface of the patient.

12. The electrotherapeutic system of claim 10, further comprising a left return electrode and a right return electrode, wherein the left return electrode is connectable to complete a current path originating from the left eyecup electrode, wherein the right return electrode is connectable to complete a current path originating from the right eyecup electrode.

13. An electrotherapeutic system for treating a visual disease, comprising:
   a signal generator configured to generate a waveform comprising a series of current pulses;
   a headband having a magnetic mount; and
   a headset having a magnetic slot configured to be mounted to the magnetic mount of the headband, wherein the headset comprises a left eyecup electrode having a contact surface with an area in a range of about 1.10 cm$^2$ to about 1.80 cm$^2$ that is positioned for contact with a skin surface within a left eye region, wherein the headset comprises a right eyecup electrode having a contact surface with an area in a range of about 1.10 cm$^2$ to about 1.80 cm$^2$ that is positioned for contact with a skin surface within a right eye region, and wherein the headset is connectable to the signal generator and configured to deliver the waveform to one or both of the left and right eyecup electrodes.

14. The electrotherapeutic system of claim 13, wherein the contact surface of each of the left and right eyecup electrodes comprises an upper contact pad and a lower contact pad.

15. The electrotherapeutic system of claim 14, wherein the upper contact pad comprises an arc that curves concave downward and the lower contact pad comprises an arc that curves concave upward.

16. The electrotherapeutic system of claim 14, wherein each of the left and right eyecup electrodes includes a mounting post, wherein the upper and lower contact pads are spaced away from the mounting post to enable contact with the applicable skin surface within the left and right eye regions.

17. The electrotherapeutic system of claim 16, wherein each of the left and right eyecup electrodes includes a plurality of upper extension arms that provide spacing between the mounting post and the upper contact pad and a plurality of lower extension arms that provide spacing between the mounting post and the lower contact pad.

18. The electrotherapeutic system of claim 13, wherein the left and right eyecup electrodes are the only components of the headset that are electrically connected to a skin surface of the patient.

19. The electrotherapeutic system of claim 13, further comprising a left return electrode and a right return electrode, wherein the left return electrode is connectable to complete a current path originating from the left eyecup electrode, and wherein the right return electrode is connectable to complete a current path originating from the right eyecup electrode.

20. An electrotherapeutic system for treating a visual disease, comprising:
- a signal generator configured to generate a waveform comprising a series of current pulses; and
- a headband having a magnetic mount; and
- a headset having a magnetic slot configured to be mounted to the magnetic mount of the headband, wherein the headset comprises a left eyecup electrode having a contact surface that is positioned for contact with a skin surface within a left eye region, wherein the headset comprises a right eyecup electrode having a contact surface that is positioned for contact with a skin surface within a right eye region, wherein the contact surface of each of the left and right eyecup electrodes comprises an upper contact pad and a lower contact pad, wherein the upper contact pad comprises an arc that curves concave downward and the lower contact pad comprises an arc that curves concave upward, and wherein the headset is connectable to the signal generator and configured to deliver the waveform to one or both of the left and right electrodes.

21. The electrotherapeutic system of claim 20, wherein the upper contact pad and the lower contact pad have a total area in a range of about 1.10 cm$^2$ to about 1.80 cm$^2$.

22. The electrotherapeutic system of claim 20, wherein each of the left and right eyecup electrodes includes a mounting post, wherein the upper and lower contact pads are spaced away from the mounting post to enable contact with the applicable skin surface within the left and right eye regions.

23. The electrotherapeutic system of claim 22, wherein each of the left and right eyecup electrodes includes a plurality of upper extension arms that provide spacing between the mounting post and the upper contact pad and a plurality of lower extension arms that provide spacing between the mounting post and the lower contact pad.

24. The electrotherapeutic system of claim 20, wherein the left and right eyecup electrodes are the only components of the headset that are electrically connected to a skin surface of the patient.

25. The electrotherapeutic system of claim 20, further comprising a left return electrode and a right return electrode, wherein the left return electrode is connectable to complete a current path originating from the left eyecup electrode, and wherein the right return electrode is connectable to complete a current path originating from the right eyecup electrode.

* * * * *